(12) United States Patent
Chen et al.

(10) Patent No.: US 6,830,899 B1
(45) Date of Patent: Dec. 14, 2004

(54) **METHOD FOR THE PRODUCTION OF PARA-HYDROXYBENZOATE IN *PSEUDOMONAS MENDOCINA***

(75) Inventors: Kevin K. Chen, Beijing (CN); Rebecca Lynn Grelak, Chadds Ford, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 717 days.

(21) Appl. No.: 09/090,044

(22) Filed: Jun. 3, 1998

Related U.S. Application Data

(60) Provisional application No. 60/049,556, filed on Jun. 13, 1997.

(51) Int. Cl.[7] .............................. C12P 1/00; C12N 9/00; C07H 21/02
(52) U.S. Cl. ........................ 435/41; 435/183; 536/23.1
(58) Field of Search ............................... 435/146, 189, 435/252.34, 253.3, 874, 877, 183; 536/23.1

(56) References Cited

U.S. PATENT DOCUMENTS

| | | | |
|---|---|---|---|
| 4,657,863 A | 4/1987 | Maxwell et al. | 435/142 |
| 4,910,143 A | 3/1990 | Vandenbergh | 435/252.34 |
| 4,968,612 A | 11/1990 | Hsieh | 435/142 |
| 5,017,495 A | 5/1991 | Yen et al. | 435/320.1 |
| 5,079,166 A | 1/1992 | Winter et al. | 435/262 |
| 5,605,823 A | 2/1997 | Yen et al. | |

FOREIGN PATENT DOCUMENTS

| | | |
|---|---|---|
| JP | 05328981 | 12/1993 |
| JP | 05336979 | 12/1993 |
| JP | 05336980 | 12/1993 |
| JP | 06078780 | 12/1993 |
| JP | 9-313193 | 12/1997 |

OTHER PUBLICATIONS

Ngo et al., "Computational Complexity, Protein Structure Prediction, and the Levinthal Paradox," in The Protein Folding Problem and Tertiary Structure Prediction, Merz, Jr., Ed., Birkhauser Boston, pp. 492–494, 1994.*
Thornton et al., "Protein engineering," Cur. Opinion Biotech., vol. 6, No. 4, pp. 367–369, Aug. 1995.*
Rudinger, p. 6 of Peptide Hormones, Parsons, Ed., University Park Press, Jun. 1976.*
Cheryl M. Wong, et al., Cloning and sequencing show that 4–hydroxybenzoate hydroxylase (PobaA) is required for uptake of 4–hydroxybenzoate in Rhizobium leguminosarum, *Chemical Abstracts*, 122, No. 5, abstract No. 48056, Jan. 30, 1995.
Romine et al., *Bioremediation of Chlorinated Polycyclic Aromatic Hydrocarbon Compounds*, 271–6 Hinchee, Robert E. Publisher: Lewis, Boca Raton, FL (1994).
Frazee, *J. Bacteriol* 175(19), 6194–202.
Romero–Steiner et al., *J. Bacteriol.* 176(18) 5771–9 (1994).
Dimarco et al., *J. Bacteriol.* 176(14), 42–77–84 (1994).
Wong et al., *Microbiology* (Reading U.K. 140(10), 2775–86 (1994).
Entsch et al., *Gene* 71(2), 279–91 (1988).
Shuman et al., *J. Biol. Chem.*, 268, 17057 (1993).
Berkel et al., *Eur. J. Biochem.* 210(2) 411–419 (1992).

\* cited by examiner

*Primary Examiner*—Ponnathapu Achutamurthy
*Assistant Examiner*—Christian L. Fronda
(74) *Attorney, Agent, or Firm*—Inna Y. Belopolsky

(57) ABSTRACT

A transformed mutant, *P. mendocina*, is provided containing a DNA fragment that inactivates all pobA genes and encodes the enzyme hydroxybenzoate hydroxylase. Mutants deficient in hydroxybenzoate hydroxylase are useful for the production of para-hydroxybenzoate (PHBA).

22 Claims, 6 Drawing Sheets

METHOD FOR THE PRODUCTION OF PARA-HYDROXYBENZOATE IN *PSEUDOMONAS MENDOCINA*

This application claims benefit of Provisional Application Ser. No. 60/049,556, filed Jun. 13, 1997.

FIELD OF INVENTION

The present invention relates to the fields of molecular biology and microbiology and the use of genetic techniques to modify existing enzymatic pathways for the production of desired compounds. More specifically, the present invention relates to a method for the production of para-hydroxybenzoate (PHBA) by a toluene-metabolizing *Pseudomonas mendocina* mutant lacking the ability to express para-hydroxybenzoate hydroxylase (PHBH).

BACKGROUND

Para-hydroxybenzoate (PHBA) is the key monomer for Liquid Crystal Polymers (LCPs) which contain approximately 67% PHBA. Esters of PHBA also can be used as backbone modifiers in other condensation polymers, i.e., polyesters, and are also used to make parabens preservatives.

Chemical synthesis of PHBA is known. For example, JP 05009154 teaches a chemical route using the Kolbe-Schmidt process from tar acid and $CO_2$ involving the extraction of tar acid from a tar naphthalene oil by an aqueous potassium hydroxide; adding phenol to the extracted tar acid potassium salt; removing $H_2O$ and reacting the resultant slurry with $CO_2$. Alternative methods of synthesis are also known; see, for example, U.S. Pat. No. 5,399,178; U.S. Pat. No. 4,740,614; and U.S. Pat. No. 3,985,797.

Chemical synthesis is problematic and costly due to the high energy needed for synthesis and extensive purification of product required. An alternate low cost method with simplified purification would represent an advance in the art. Biological production offers one such low cost, simplified solution to this problem.

Microbiological methods of PHBA synthesis are known. For example, JP 06078780 teaches PHBA preparation by culturing benzoic acid in the presence of microorganisms (preferably Aspergillus) that oxidize benzoic acid to PHBA.

An alternate method of biological production is suggested by bacteria that have an enzymatic pathway for the degradation of toluene and other organics where PHBA is produced as an intermediate. The first enzyme in the toluene degradation pathway is toluene monooxygenase (TMO) and the pathway is referred to as the TMO pathway. Bacteria that possess the TMO pathway are primarily restricted to the genus Pseudomonas where *P. putida, P. fluorescens, P. aeruginosa* and *P. mendocina* are the most commonly utilized species. The TMO pathway has been highly characterized [Romine et al., *Bioremediation of Chlorinated Polycyclic Aromatic Hydrocarbon Compounds* (1994), 271–6. Editor(s): Hinchee, Robert E. Publisher: Lewis, Boca Raton, Fla.] and a number of the genes encoding key enzymes have been cloned and sequenced, including the protocatechuate 3,4-dioxygenase genes [Frazee, *J. Bacteriol.*, (1993), 175 (19), 6194–202], the pcaR regulatory gene from *Pseudomonas putida*, which is required for the complete degradation of p-hydroxybenzoate [Romero-Steiner et al., *J. Bacteriol.* (1994), 176(18), 5771–9; Dimarco et al., *J. Bacteriol.* (1994), 176(14), 4277–84] and the pobA gene encoding the expression of para-hydroxybenzoate hydroxylase (PHBH), the principal enzyme for the conversion of PHBA to protocatechuate [Wong et al., *Microbiology* (Reading U.K.) (1994), 140(10), 2775–86; Entsch et al., *Gene* (1988), 71(2), 279–91].

Bacteria that possess the TMO pathway are useful for the degradation of toluene and trichloroethylene and are able to use these and other organics as sole carbon sources where they are transformed through PHBA to ring opening degradation products (U.S. Pat. No. 5,017,495; U.S. Pat. No. 5,079,166; U.S. Pat. No. 4,910,143).

Recently, various strains of Pseudomonas possessing the TMO pathway have been used to produce muconic acid via manipulation of growth conditions (U.S. Pat. No. 4,657,863; U.S. Pat. No. 4,968,612). Additionally, strains of Enterobacter with the ability to convert p-cresol to PHBA have been isolated from soil (JP 05328981). Further, JP 05336980 and JP 05336979 disclose isolated strains of *Pseudomonas putida* with the ability to produce PHBA from p-cresol.

Although the above cited methods are useful for the production of PHBA, these methods are limited by the high cost and toxicity of the aromatic substrate, p-cresol. Furthermore, the above methods use an isolated wildtype organism that converts part of the p-cresol to PHBA while the rest is further metabolized. The utility of these methods are therefore limited by low yields and an inability to control further degradation of the desired product.

Shuman et al., (*J. Biol. Chem.*, (1993), 268, 17057) have reported the identification of a gene encoding a putative isozyme of PHBH from *P. fluorescens*. The comparison of the deduced amino acid sequence from this gene with the enzyme encoded by the more fully characterized pobA gene of *P. fluorescens* (van Berkel et al., *Eur. J. Biochem.*, (1992), 210 (2), 411–419) demonstrates 73% homology with the isozyme. Although the work of Shuman et al. (supra) suggest the presence of a second gene encoding an alternate PHBH, the authors were not able to isolate any expressed protein and concluded that the gene encoding the isozyme is not expressed.

Therefore, the problem to be overcome is to develop a method of microbially mediated PHBA production from an inexpensive, aromatic substrate, where the microbial TMO pathway has been altered to prevent the degradation of PHBA.

SUMMARY OF THE INVENTION

The present invention provides a method for the production of PHBA comprising: (i) culturing a pobA(−) Pseudomonas strain in a medium containing an aromatic organic substrate, at least one suitable carbon source, and a nitrogen source, wherein the pobA(−) Pseudomonas strain comprises genes encoding the TMO toluene degradation pathway and wherein the pobA(−) Pseudomonas strain does not produce any detectable para-hydroxybenzoate hydroxylase, whereby PHBA accumulates; and (ii) recovering the PHBA.

The invention further provides genes encoding novel para-hydroxybenzoate hydroxylase enzymes and pobA(−) Pseudomonas strains deficient in hydroxybenzoate hydroxylase that are able to accumulate PHBA under suitable growth conditions and in the presence of a suitable aromatic substrate.

BRIEF DESCRIPTION OF BIOLOGICAL DEPOSITS AND SEQUENCE LISTING

Figure 1A:
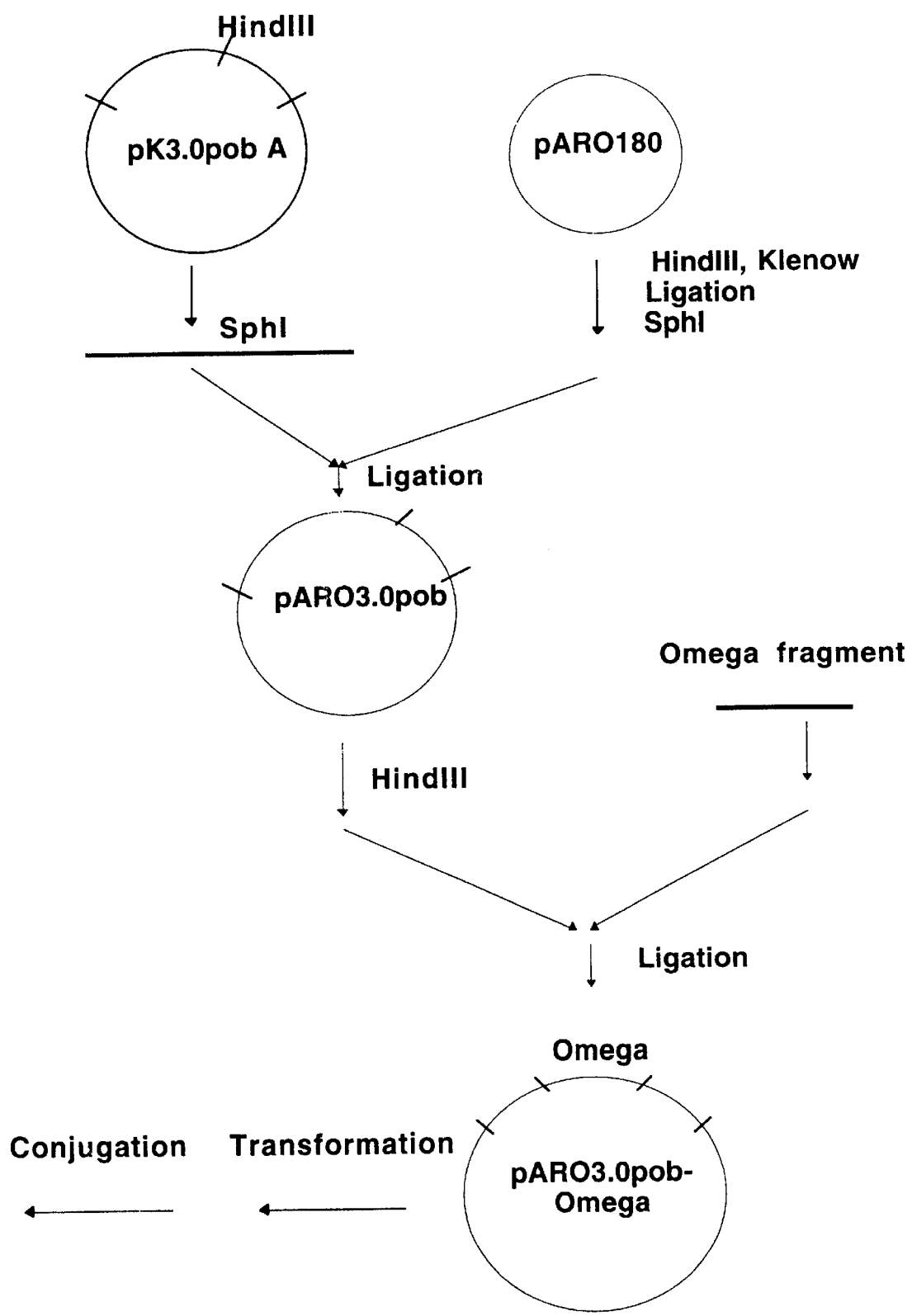
FIG. 1(*a*) schematically represents plasmid vectors used for the disruption of pobA-1 alone in the variant of *P. mendocina*.
FIG. 1(b) schematically represents plasmid vectors used for the disruption of pobA-1 and pobA-2 in the variant of P. mendocina.

The transformed P. mendocina KRC1651 containing the omega-disrupted pobA-1 and pobA-2 genes was deposited on Nov. 26, 1996, with the ATCC under the terms of the Budapest Treaty on the International Recognition of the Deposit of Microorganisms for the Purposes of Patent Procedure and is designated as ATCC 55885.

The fast-growing P. mendocina KRC16 was deposited on Nov. 26, 1996 with the ATCC under the terms of the Budapest Treaty on the International Recognition of the Deposit of Microorganisms for the Purposes of Patent Procedure and is designated as ATCC 55886.

"ATCC" refers to the American Type Culture Collection international depository located at 10801 University Boulevard, Manassas, Va. 20110-2209, U.S.A. The designations refer to the accession number of the deposited material.

Applicant(s) have provided sequence listings in conformity with 37 C.F.R. 1.821–1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions).

SEQ ID NO: 1 gives the nucleotide sequence of the pobA-1 gene isolated from P. mendocina KR-1.

SEQ ID NO: 2 gives the nucleotide sequence of the pobA-2 gene isolated from P. mendocina KR-1.

SEQ ID NO: 3 gives the amino acid sequence of the pobA-1 gene isolated from P. mendocina KR-1.

SEQ ID NO: 4 gives the amino acid sequence of the pobA-2 gene isolated from P. mendocina KR-1.

SEQ ID NO: 5 gives the nucleotide sequence of the pobA gene isolated from P. fluorescens (van Berkel et al., supra.)

SEQ ID NO: 6 gives the nucleotide sequence of the pobB gene encoding the PHBH isozyme isolated from P. fluorescens (Shuman et al., supra.)

SEQ ID NO: 7 gives the amino acid sequence of the pobA gene isolated from P. fluorescens (van Berkel et al., supra.)

SEQ ID NO: 8 gives the amino acid sequence of the pobB gene encoding the PHBH isozyme isolated from P. fluorescens (Shuman et al., supra.)

SEQ ID NO:9 gives the nucleotide sequence of the 5' primer used to generate the pobA hybridization probe for the isolation of the pobA-1 and pobA-2 genes.

SEQ ID NO: 10 gives the nucleotide sequence of the 3' primer used to generate the pobA hybridization probe for the isolation of the pobA-1 and pobA-2 genes.

DETAILED DESCRIPTION OF THE INVENTION

Applicants have developed a fast-growing P. mendocina mutant which lacks the PHBH enzyme and is unable to convert PHBA to PCA. The mutant metabolizes toluene and p-cresol resulting in the accumulation of PHBA in the growth medium. Applicants have made the unexpected finding that P. mendocina posseses two, highly homologous pobA genes, both of which encode enzymes able to convert PHBA to PCA.

Applicants have also provided a method for the biological production of PHBA from genetically altered Pseudomonas. The method provides PHBA without the high energy cost of synthetic production and without producing toxic waste streams. PHBA is a valuable monomer for the synthesis of liquid crystalline polymers.

The following definitions are to be used to interpret the terms contained in the claims and specification.

The terms "plasmid" and "vector" refer to an extra chromosomal element often carrying genes which are not part of the central metabolism of the cell, and usually in the form of circular double-stranded DNA molecules. Such elements may be autonomously replicating sequences, genome-integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation vector" refers to a specific vector containing a foreign gene and having elements in addition to the foreign gene that facilitate transformation of a particular host cell.

A "fragment" constitutes a fraction of the DNA sequence of the particular region.

The term "transformation" refers to the acquisition of new genes in a cell after the incorporation of nucleic acid.

The term "expression" refers to the transcription and translation to gene product from a gene coding for the sequence of the gene product. In the expression, a DNA chain coding for the sequence of gene product is first transcribed to a complimentary RNA which is often a messenger RNA and, then, the transcribed messenger RNA is translated into the above-mentioned gene product if the gene product is a protein.

The terms "restriction endonuclease" and "restriction enzyme" refer to an enzyme which binds and cuts within a specific nucleotide sequence within double-stranded DNA. "Polymerase Chain Reaction" and "PCR" refer to a method that results in the linear or logarithmic amplification of nucleic acid molecules. PCR generally requires a replication composition consisting of, for example, nucleotide triphosphates, two primers with appropriate sequences, DNA or RNA polymerase and proteins. These reagents and details describing procedures for their use in amplifying nucleic acids are provided in U.S. Pat. No. 4,683,202 (1987, Mullis et al.) and U.S. Pat. No. 4,683,195 (1986, Mullis et al.).

"Gene" refers to a nucleic acid fragment that expresses a specific protein, including regulatory sequences preceding (5' non-coding) and following (3' non-coding) the coding region. "Native" gene refers to an isolated gene with its own regulatory sequences as found in nature. "Chimeric gene" refers to a gene that comprises heterogeneous regulatory and coding sequences not found so assembled in nature. "Endogenous" gene refers to the native gene normally found in its natural location in the genome and is not isolated.

"TMO" is the abbreviation for toluene monooxygenase-1.

The terms "TMO degradative pathway" or "TMO enzymatic pathway" refer to the enzymes and genes encoding the enzymes found in some Pseudomonas bacteria that are responsible for the degradation of toluene and similar aromatic substrates. The TMO pathway is outlined in FIG. 4 and contains at least toluene-4-monooxygenase, p-cresol methylhydroxylase, p-hydroxybenzoaldehyde dehydrogenase, and p-hydroxybenzoate hydroxylase.

"PHBH" is the abbreviation for para-hydroxybenzoate hydroxylase, the enzyme in the TMO pathway responsible for the conversion of PHBA to PCA.

"PHBA" is the abbreviation for para-hydroxybenzoate which is also known as para-hydroxybenzoic acid or 4-hydroxybenzoic acid.

"PCA" is the abbreviation for protocatechuic acid.

"EDTA" is the abbreviation for ethylenediaminetetraacetic acid.

The term "pobA" refers to a gene encoding the para-hydroxybenzoate hydroxylase enzyme.

The term "pobB" refers to the gene encoding the putative isozyme of PHBH from P. fluorescens.

"pobA-1" refers to a first gene encoding para-hydroxybenzoate hydroxylase and having the sequence as given by SEQ ID NO: 1 and is contained within a 3.0 kb fragment of P. mendocina genomic DNA isolated by hybridization using a pobA hybridization probe. "pobA-2" refers to a second gene encoding para-hydroxybenzoate hydroxylase and having the sequence as given by SEQ ID NO:2 and is contained within a 4.5 kb fragment of P. mendocina genomic DNA isolated by hybridization using a pobA hybridization probe.

"pobR" refers to a transcriptional activator gene required for the expression of pobA genes in Pseudomonas sp.

The term "pobA hybridization probe" refers to a 1.2 kb PCR amplification product produced by amplification of P. mendocina genomic DNA with primers based on the nucleotide sequence of the P. fluorescens pobA gene [SEQ ID NO: 5] as described by van Berkel et al., Eur. J Biochem. (1992), 210 (2), 411–419.

The term "pobA(−) Pseudomonas" refers to a genetically manipulated Pseudomonas having mutations or disruptions in all pobA genes such that the genetically manipulated Pseudomonas is unable to produce active para-hydroxybenzoate hydroxylase.

The term "aromatic organic substrate" refers to an aromatic compound that is degraded by the TMO enzymatic pathway. Typical examples of suitable aromatic substrates are toluene and p-cresol.

The term "carbon source" refers to a substrate suitable for bacterial cell growth that is distinct from the aromatic substrate. Suitable carbon substrates include but are not limited to glucose and succinate.

The term "TMO P. mendocina variant" refers to a genetic variant of a wildtype P. mendocina capable of metabolizing toluene and demonstrating an increase in cell density of at least 6 fold greater than the wildtype under growth conditions of approximately 160 ppm toluene as a sole carbon source. Variants are typically produced by standard mutagenic methods and screened for higher growth rate and the ability to metabolize toluene and other aromatic substrates.

The term "suicide vector" refers to a vector generally containing a foreign DNA fragment to be expressed in a suitable host cell, coupled with a genetic element that will be lethal to the host cell unless the cell is able to express the foreign DNA. "Suicide vector" is also understood to mean a non-replicating vector capable of transfecting a host cell and facilitating the incorporation of foreign DNA into the genome of the host cell. Such a vector does not replicate and is thus destroyed after incorporation of the heterologous DNA. Examples of common suicide vectors and their construction may be found in (Sambrook et al., Molecular Cloning: A Laboratory Manual—volumes 1,2,3 (Cold Spring Harbor Laboratory: Cold Spring Harbor, N.Y., 1989)).

The term "Kam" refers to a gene encoding Kanamycin resistance.

The term "Amp" refers to a gene encoding Ampicillin resistance.

The term "Strep" refers to a gene encoding Streptomycin resistance.

Applicants' method involves mutagenesis of a toluene-metabolizing P. mendocina strain such that the mutant strain demonstrates a cell density of at least 6 fold greater than the wildtype under growth conditions of approximately 160 ppm toluene. The fast-growing TMO varient was then genetically altered so that all genes encoding para-hydroxybenzoate hydroxylase (PHBH) were disrupted. P. mendocina strains containing the disrupted genes (pobA-1, pobA-2), referred to as pobA (−) mutants, were then grown in the presence of toluene or p-cresol and PHBA was accumulated in the medium.

Creation of pobA(−) mutants proceeded by (i) the isolation of a pobA hybridization probe; (ii) isolation of pobA-1 from a TMO variant using the probe; (iii) disruption of pobA-1 using an omega element and subsequent cloning and expression into a suicide vector which confirmed the existence of an alternate pathway for PHBA catabolism; (iv) isolation of pobA-2; (v) disruption of both pobA-1 and pobA-2; and (vi) cloning into a suicide vector for the creation of a pobA (−) mutant TMO variant that accumulates PHBA in the presence of toluene or p-cresol and an alternate carbon source.

One of the most significant aspects in the development of the present method is the discovery that the instant strains contained two expressed pobA genes, both of which needed to be inactivated before PHBA accumulation could be effected. Another significant aspect of the invention is the creation of a toluene-metabolizing P. mendocina strain that has a significantly higher rate of growth and metabolism than many toluene-metabolizing strains known in the art. The fast-growing TMO variant provides a host useful for the commercial production of PHBA and that permits rapid screening of pobA(−) transformants.

Production Conditions

TMO-Containing Bacterial Strains

Bacterial cells preferred in the present invention are those that possesses the TMO pathway. Such strains are generally restricted to the genus Pseudomonas and include but are not limited to P. putida, P. fluorescens, P. aeruginosa and P. mendocina.

Figure 4:
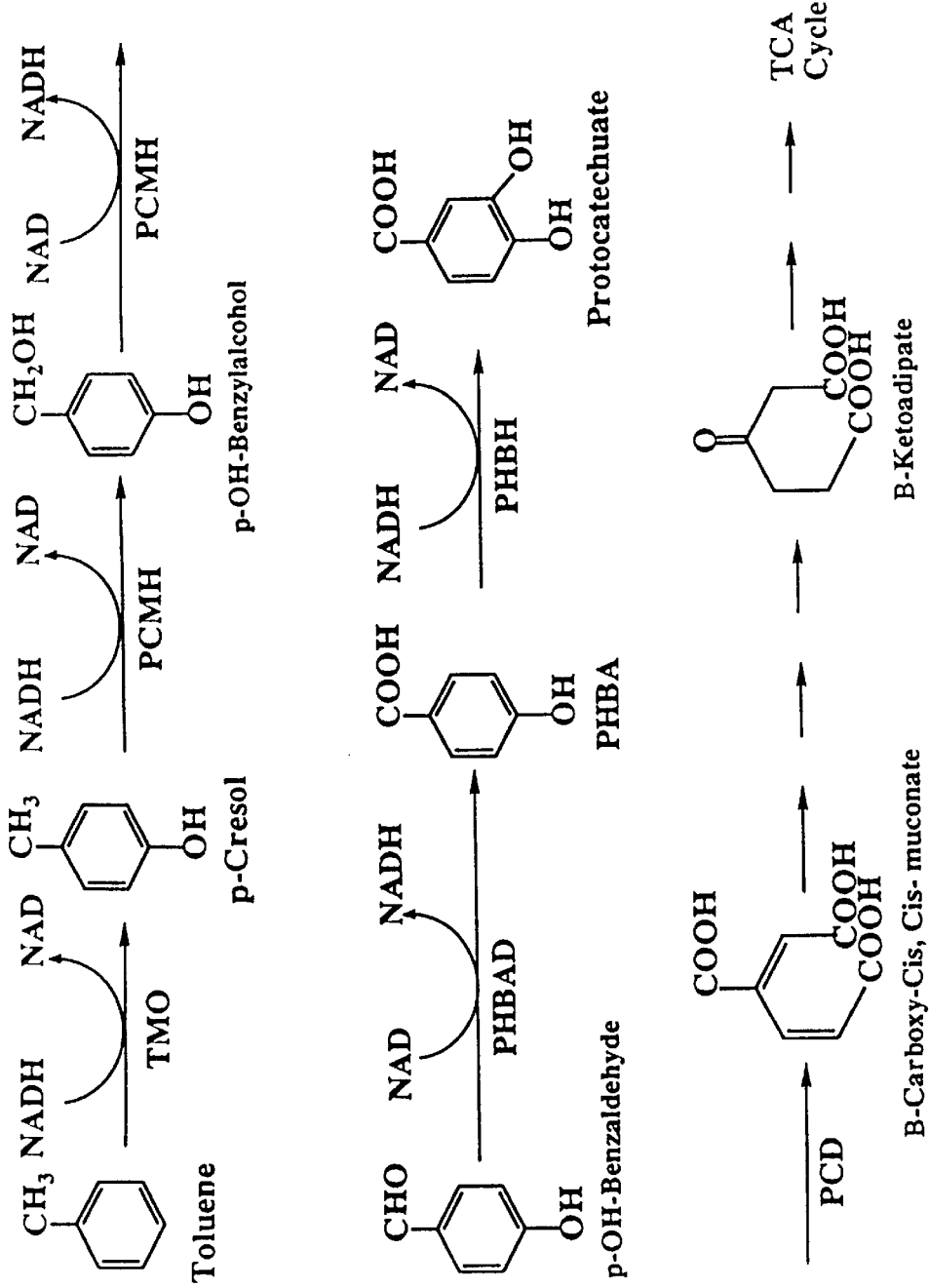
FIG. 4 schematically shows the TMO enzymatic pathway.

Strains of Pseudomonas containing the TMO pathway are known to oxidize toluene to form intermediates of the tricarboxylic acid cycle. PHBA as well as other intermediates, such as p-cresol, p-hydroxybenzyl alcohol and p-hydroxybenzadehyde, are formed in the upper pathway, which metabolizes toluene to the ring cleavage substrate (FIG. 4). In wildtype Pseudomonas strains, PHBA is immediately converted to protocatechuate (PCA) as it is formed. The biochemistry of the enzymes involved in the upper pathway have been described for several Pseudomonas strains (Romine et al., supra).

Batch and Continuous Fermentations

The present process uses a batch method of fermentation. A classical batch fermentation is a closed system where the composition of the medium is set at the beginning of the fermentation and not subjected to artificial alterations during the fermentation. Thus, at the beginning of the fermentation the medium is inoculated with the desired organism or organisms and fermentation is permitted to occur adding nothing to the system. Typically, however, a batch fermentation is "batch" with respect to the addition of carbon source and attempts are often made at controlling factors such as pH and oxygen concentration. In batch systems the metabolite and biomass compositions of the system change constantly up to the time the fermentation is stopped. Within batch cultures, cells moderate through a static lag phase to a high growth log phase and finally to a stationary phase where growth rate is diminished or halted. If untreated, cells in the stationary phase will eventually die.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the medium. An advantage of the Fed-Batch system is that it is more amenable to the use of toxic or immiscible aromatic substrates such as toluene. Using a Fed-Batch system it is possible to maintain a steady concentration of substrate at non-toxic levels while accommodating maximum bioconversion of the substrate to product.

The production of PHBA from aromatic compounds such as toluene will be limited by the amount of the aromatic substrate and carbon sources added. In simple Batch fermentation, production will be limited by the amount of toluene initially added. Since toluene is toxic and has limited solubility in water, its low initial concentration will govern the amount of PHBA produced. The ability to run the process at such a low toluene (i.e., 30–60 ppm) allows operation below a lower explosive limit which for toluene is 120 ppm. This is a clear safety advantage to the process. Fed-Batch techniques where the carbon source and toluene are added at rates which are similar to the utilization of these compounds will keep the toluene concentration in the medium low and can significantly increase the amount of PHBA produced.

Batch and Fed-Batch fermentations are common and well known in the art and examples may be found in, for example Thomas D. Brock in Biotechnology: *A Textbook of Industrial Microbiology*, Second Edition (1989) Sinauer Associates, Inc., Sunderland, Mass., or Deshpande, Mukund V. *Appl. Biochem. Biotechnol.* 36, 227, (1992).

Although the present invention is performed in batch mode, it is contemplated that the method would be adaptable to continuous fermentation methods. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen source at low concentration and allow all other parameters to be in excess. In other systems a number of factors affecting growth can be altered continuously while the cell concentration, measured by medium turbidity, is kept constant. Continuous systems strive to maintain steady state growth conditions and thus the cell loss due to medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, Fed-Batch or continuous processes and that any known mode of fermentation would be suitable. Additionally, it is contemplated that cells may be immobilized on a substrate as whole cell catalysts and subjected to fermentation conditions for PHBA production.

Fermentation Studies and Culture Conditions

The present invention provides a process for the production of PHBA in a culture medium by *P. mendocina* comprising culturing a genetically engineered *P. mendocina* host having no p-hydroxybenzoate hydroxylase where all pobA genes are disrupted. The medium may optionally contain a nitrogen source, minor metals, a carbon source and an aromatic substrate. The culture medium can contain any inorganic or organic source of nitrogen normally used in processes for culturing microorganisms. Nitrogen sources may be either inorganic (ammonium salts, e.g., ammonium sulfate) or organic nitrogen (e.g., yeast extract).

Growth Conditions

Typically, cells are cultured in flasks and fermenters and the fermentation modes used were batch, Fed-Batch and continuous. Both "rich" and "lean" media were used as described in the GENERAL METHODS. Culture conditions were modulated according to the method of growth and optimized for the production of PHBA. The pH of the cultures should be maintained within a range of about from 6.3 to 7.9 wherein a range from about 7.2 to 7.7 is most preferred. Methods for the optinization of cell growth and metabolism are well known in the art, for example as described in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994).

Carbon Source

A variety of carbon sources are suitable in the present invention and include but are not limited to materials such as succinate, lactate, acetate, ethanol, monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. The choice of the carbon substrate will be determined by the needs of the desired production cell. For the purposes of the present invention, glucose is preferred.

In pobA(-) *P. mendocina* cultures, a carbon source is necessary as the TMO pathway is completely blocked, and the strain is not able to utilize the aromatic substrate as a carbon source for the production of energy. In practice, it is necessary to balance the concentration of the carbon substrate against the concentration of the aromatic substrate in order to control the amount of oxidation of the aromatic substrate at the beginning of the TMO pathway.

Aromatic substrates

A variety of aromatic substrates may be used in the present invention, including but not limited to toluene, p-cresol, p-hydroxybenzyl alcohol, p-hydroxybenzaldehyde, benzoate and any aromatic compounds where the chemical structure is similar to toluene and the intermediates of the TMO pathway.

The production of PHBA from aromatic substrates such as toluene and p-creosol will be limited by the concentration of the substrate and the carbon source in the medium. Preferred concentrations of toluene are from about 30 ppm to about 500 ppm where a range of about 30 ppm to about 60 ppm is most preferred and a range of about 30 ppm to 60 ppm is most preferred. Preferred concentrations of p-creasol are from about 1 mM to about 5 mM.

Cloning and Sequencing of 12pobA-1 Gene

Development of fast-growing TMO *P. mendocina* variant

The present invention provides a fast-growing Pseudomonas strain that exhibits a cell density of at least 6 fold greater than the wildtype under growth conditions of 0.2% toluene. The fast-growing strain is referred to as a TMO variant. Preferred Pseudomonas strains will be those that are able to metabolize toluene and possess the key enzymes in the TMO enzymatic pathway (FIG. 4). Strains known to possess this pathway and useful in the present invention include but are not limited to *P. putida, P. fluorescens, P. aeruginosa* and *P. mendocina*. Most preferred are the *P. mendocina* strains KRC16 (ATCC 55886) and KRC50.

The TMO variant was developed by U.V. mutagenesis of a *P. menodcina* strain (KR-1) (Amgen, U.S. Pat. No. 5,171, 684) known to be able to use toluene as a sole carbon source. After mutagenesis, cells were plated on a standard medium containing toluene and colonies were picked on the basis of size and speed of development. In this fashion KRC50 was isolated. A second mutation of KRC50 produced KRC16 (ATCC 55886) which exhibited a cell density of at least 6 fold higher than the parent KR-1 under growth conditions of approximately 160 ppm toluene. KRC16 was then used for further genetic studies.

Methods of mutagenesis useful in the invention are not limited to the use of U.V. light protocols but encompass a variety of agents such as chemical agents including $HNO_2$ and $NH_2OH$, as well as compounds that affect replicating DNA such as acridine dyes, notable for causing frameshift mutations. Specific methods for creating mutants using radiation or chemical agents are well documented in the art. See, for example, Brock, supra.

Isolation of pobA-1 with a pobA hybridization probe

Identification of the pobA-1 gene in the TMO variant KRC16 (ATCC 55886) proceeded by first amplifying genomic DNA from KRC16 with primers designed from the known base sequence of pobA isolated from *P. fluorescens* (van Berkel et al., supra). PCR amplification (U.S. Pat. No. 4,683,202 (1987, Mullis et al.) and U.S. Pat. No. 4,683,195 (1986, Mullis et al.) produced a 1.2 kb fragment that was used to probe KRC16 genomic DNA. Analysis of the genomic DNA by Southern blot (Southern, *J. Mol. Biol.* 98, 503, (1975)) revealed two bands by gel electrophoresis. One band, migrated at about 3.0 kb and the other migrated at 4.5 kb. The 3.0 kb band was excised and used for cloning and sequencing. Sequence analysis revealed the base sequence of pobA-J as given in SEQ ID NO: 1. Comparison of the deduced amino acid sequence from the base sequence of pobA-1 [SEQ ID NO:3] with the known peptide encoded by the pobA gene of *P. fluorescens* [SEQ ID NO:7] (van Berkle et al., supra) show 68% similarity suggesting pobA-1 encodes *P. mendocina* PHBH.

Cloning pobA-1 gene and confirmation of expression

The 3.0 kb fragment was re-isolated from agarose gel and cloned into an appropriate vector for transformation into E. co/i in order to confirm pobA-1 expression of active PHBH. Vectors suitable for the transformation of *E. coli* are numerous and well known in the art. Suitable vectors can be derived, for example, from a bacterium, a virus (such as bacteriophage T7 or a M-13 derived phage), a cosmid, a yeast or a plant. Protocols for obtaining and using such vectors are known to those in the art. (Sambrook et al. Molecular Cloning: A Laboratory Manual—volumes 1,2,3 (Cold Spring Harbor Laboratory: Cold Spring Harbor, N.Y., 1989)).

PobA-1 was cloned into a sphI site of a pUC18 vector (Parke, D., *Gene* (1990), 93(1), 135–7), creating pUC3.OK which was used to transform the *E. coli* strain DH5α. Transformants were screened for inserts containing the 3.0 kb fragment. Positive transformants were then grown in the presence of PHBA and toluidine to test for the expression of active PHBH by pobA-1. Conversion of PHBA to PCA was indicated by a colored reaction product formed by the reaction of toluidine and PCA. This method of assay is common and well known in the art; see, for example, "Application of p-Toluidine in Chromogenic Detection of Catechol and Protocatechuate, Diphenolic Intermediates in Catabolism of Aromatic Compounds" (Parke, *Applied and Environmental Microbiology*, August 1992, P.2694–2697).

Disruption of pobA-1

Cloning of the 3.0 kb pobA-1 gene fragment into suicide vector

In order to clone the pobA-1 gene into a suicide vector amenable to manipulation for gene disruption, the 3.0 kb fragment was re-isolated from pUC3.0k and cloned into the sphI site of the suicide vector, pARO180 (Park, D., supra) to form the vector pARO3.0pobA. (FIG. 1(*a*))

Construction of suicide vectors are common and well known in the art and have been developed to transfect a variety of microorganisms to facilitate genetic manipulations. For example, suicide vectors capable of transfecting Salmonella (Galen et al., 96th General Meeting of the American Society for Microbiology, New Orleans, La., USA, May 19–23, 1996. Abstracts of the General Meeting of the American Society for Microbiology 96 (0), (1996) 529); Streptococcus (Brooker et al., *Letters in Applied Microbiology* 21 (5) (1995) 292–297); Rhizobium (Safronova et al., *Genetika* 30 (6) (1994) 763–768); Rhodobacter (Penfold et al., *Gene* (Amst) 118 (1) (1992) 145–146) and other gram-negative bacteria (Skrzypek et al., *Plasmid* 29 (2) (1993) 160–163), have all been constructed. Suicide vectors will be constructed so as to accommodate the specific host to be transfected and to accomplish the desired purpose. Generally suicide vectors useful in the present invention are non-replicating and capable of transfecting a host cell with foreign DNA and facilitating incorporation of that DNA into the genome of the host cell. Such vectors are destroyed after transfecting the desired host with foreign DNA.

Within the context of the present invention, a mobilizing, narrow host range vector, which will replicate to high copy number in *E. coli* is preferred. Such vectors will be able to be efficiently transferred to other gram-negative bacteria from a mobilizing host strain such as S17-1 (Parke et al., supra). For the purposes of the present invention a variety of suicide vectors will serve to carry the pobA gene for transfection into a suitable host where pARO180 is preferred.

Disruption of pobA-1 gene with Omega element

In order to prevent expression of the cloned pobA-l gene, a nucleic acid disrupting fragment known as an omega element was cloned into a HindIII site within the coding region of the pobA-1 gene on the vector pARO3.0pobA. The omega element carries a gene for Streptomycin resistance and is fully described in Prentki et al., Gene 29, 303, (1984). The vector containing the disrupted pobA-1 was then used to transform a mobilizing E. coli strain for eventual transfer into the P. mendocina KRC16 (ATCC 55886).

The process of gene disruption analysis is common and well known in the art. Gene disruption involves inserting a non-coding DNA fragment or a DNA fragment of a selectable marker in the coding region of a target structural gene and transforming a host containing an endogenous target gene with that disrupted construct. Homologous recombination between the disrupted gene and the endogenous gene will result in inactivation of the endogenous gene in the host organism. Gene disruption is used in a variety of organisms such as Mycobacterium (Balasubramanian et al., Journal of Bacteriology 178 (1) (1996) 273–279); Saccharomyces (Daran et al., European Journal of Biochemistry 233 (2) (1995) 520–530); Brevibacterium (Su Y -C et al., Proceedings of the National Science Council Republic of China Part B, Life Sciences 19 (2) (1995) 113–122); as well as E. coli (Cherepanov et al., Gene (Amsterdam) 158 (1) (1995) 9–14).

To transfer the plasmid containing the disrupted pobA-1 gene to KRC16 (ATCC 55886), the transformed mobilizing E. coli was incubated in a 1:4 ratio with KRC16 and plated on a standard medium. Positive transformants were selected on the basis of antibiotic resistance and the presence of the disrupted pobA-1 gene was confirmed by re-isolation of the gene by restriction analysis and hybridization with the 1.2 kb pobA hybridization probe. This process is called transformation by conjugation. Alternatively, cells may be transformed by known procedures such as by protocols involving calcium-permeabilized cells, electroporation, or by transfection using a recombinant phage virus. (Sambrook et al., supra)

The disrupted pobA-1 gene is an integrating DNA fragment which has a DNA sequence with homology to a target site in the genome of the host cell so that the chimerical DNA fragment of pobA-1 gene and a drug-resistance gene can be integrated into the genome of the host P. mendocina. Analysis of PHBA Conversion with pobA-1 Disrupted Strains Transformed KRC16 (ATCC 55886) carrying the disrupted pobA-1 gene was grown in the presence of toluene or p-cresol under suitable conditions for the production of PHBA. Analysis of the culture supernatant by GC/Mass spectrometry indicated that only marginal PHBA accumulation occurred while there was significant production of PCA. These data suggested that the disruption of pobA-1 did not block the TMO pathway at the PHBH step and that the P. mendocina KRC16 (ATCC 55886) mutant carrying the disrupted pobA-1 gene was still capable of converting PHBA to PCA.

Since the initial analysis of KRC16 genomic DNA had indicated a 4.5 kb fragment resulting from hybridization with the pobA probe, in addition to the 3.0 kb fragment, it was decided to investigate whether this 4.5 kb fragment represented an alternate pobA gene capable of mediating the conversion of PHBA to PCA in the presence of a disrupted pobA-1 gene.
Construction of a P. mendocina KRC16 Containing Two Disrupted pobA Genes
Isolation, disruption and cloning of pobA-2
The 4.5 kb fragment was isolated from a gel following restriction of P. mendocina genomic DNA and probing with the pobA hybridization probe, essentially in the same fashion as the isolation of the 3.0 kb fragment. The isolated gene was referred to as pobA-2. Sequence analysis revealed the base sequence of pobA-2 as given in SEQ ID NO:2. Comparison of the deduced amino acid sequence from the base sequence of pobA-2 [SEQ ID NO:4] with the known peptide encoded by the pobB gene for a putative PHBH isozyme [SEQ ID NO:8] of P. fluorescens (Shuman et al., supra) show 71.2% similarity suggesting pobA-2 encodes P. mendocina PHBH.

Disruption of pobA-2

In order to create a disrupted pobA-2 gene the isolated pobA-2 gene was cloned into a pUC4K vector (Pharmacia Biotech, Piscataway, N.J., 08854, USA) and then the gene was disrupted by the insertion of a Kam resistance gene cassette into an Eco47III site in the pobA-2 gene. The resulting plasmid was termed pK4.5pobA-Kam (FIG. 1(b)). Digestion of pK4.5pobA-Kam with sphI and subsequent ligation with the suicide vector pARO180 produced pAR04.5pob-Kam. pAR04.5pob-Kam was moved into a mobilizing E. coli strain and KRC16, containing the omega-disrupted pobA-1 gene was transformed. A number of transformants were selected and found to contain the disrupted pobA-2 gene. Eight strains (KRC1615, KRC1616, KRC1651 (ATCC 55885), KRC1617, KRC1645, KRC1652, KRC1653, and KRC1657) were selected for further study. The presence of both disrupted genes was confirmed by re-isolation of the genes by restriction analysis and hybridization with the 1.2 kb pobA hybridization probe.
PHBA Accumulation in KRC1615, KRC1616, KRC1651 (ATCC 55885) KRC1617, KRC1645, KRC1652, KRC1653, AND KRC1657

Figure 3:
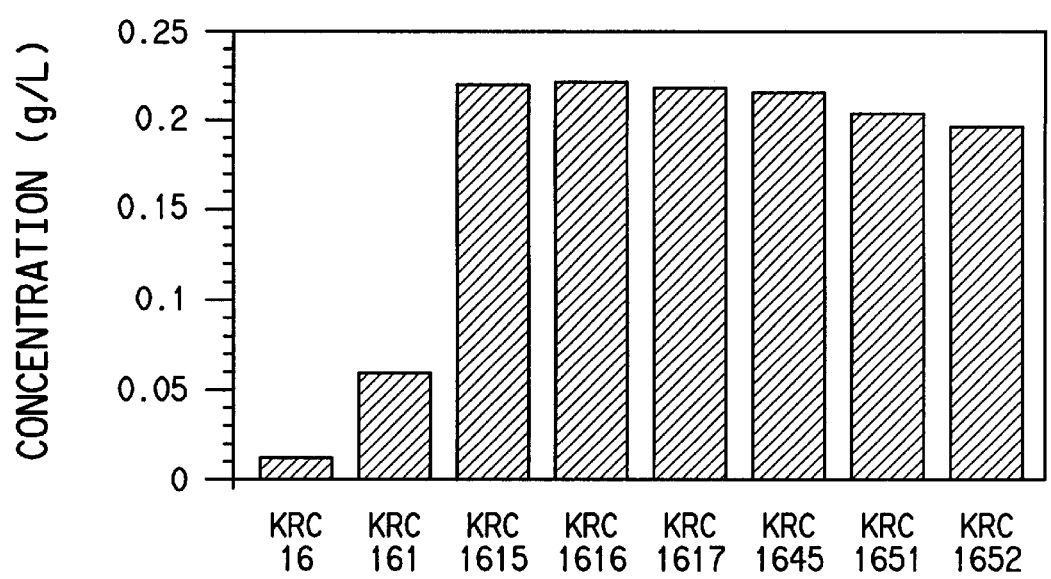
FIG. 3 graphically compares the accumulation of PHBA in the pobA (–) P. mendocina mutants.

Eight P. mendocina strains, (KRC1615, KRC1616, KRC1651 (ATCC 55885), KRC1617, KRC1645, KRC1652, KRC1653, and KRC1657), containing disrupted pobA-1 and pobA-2 genes, were grown in the presence of toluene or p-cresol and an alternate carbon source and the culture supernatant was analyzed for accumulation of PHBA and PCA. Analysis by GC/MS indicated that no PCA was formed. KRC1651 (ATCC 55885) appeared to be the highest producer of PHBA. A comparison of the relative PHBA production of all strains is seen in FIG. 3. Methods of PHBA Assay PHBA may be detected by a variety of means including Gas chromatography coupled with Mass spectrophotometry (GC/MS) or methods using capillary electrophoresis and HPLC. Capillary electrophoresis is preferred for rapid analysis where a large number of samples are involved, whereas GC/MS is noted for its sensitivity, accuracy and the ability to confirm the correct chemical structure of the compound being characterized.

Methods for determining the existence of PHBA and toluene derivatives by GC/MS are known in the art (see, for example, Adachi et al., Meijo Daigaku Nogakubu Gakujutsu Hokoku (1996) 32, 53–57; Luczak et al., Fitoterapia (1991) 62(5), 455–6; Uda et al., Nippon Shokuhin Kogyo Gakkaishi (1988) 35(5), 360–6). The present methods are based on those of the literature and are more fully described in the GENERAL METHODS.

Methods for determining PHBA by capillary electrophoresis are also known in the art (see, for example, Chen et al., Fenxi Huaxue (1995) 23(11), 1281–3; Wu et al., J Chromatogr., A (1995) 716(1+2), 291–301). Capillary electrophoresis may be used in the present invention to detect PHBA as well as the disappearance of toluene and p-cresol from the culture supernatant of a pobA(-) P. mendocina strain.

Capillary electrophoresis uses a combination of electrophoretic migration and electroosmotic flow to separate molecules based on differences in charge, size, isoelectric focusing and hydrophobicity.

Regulation of the pobR Repressor

Although the foregoing describes only the genetic manipulation of the pobA gene in the *P. mendocina* TMO pathway, it is contemplated that other regulatory genes may also be manipulated to effect PHBA and other TMO intermediate metabolite accumulation. One such regulatory gene is the pobR gene.

pobR is a transcriptional activator required for the expression of pobA gene (DiMarco et al., *J Bacteriol.* (1993) 175(14), 4499–506; DiMarco et al., *J Bacteriol.* (1994) 176(14), 4277–84). Applicants have isolated and sequenced two pobR genes from *P. mendocina* KRC16, which are located upstream of pobA-1 and pobA-2. It is possible that each pobA gene in *P. mendocina* contains a region which may be involved in sequence-specific recognition by pobR, forming the core of the operator site as reported in *Acinetobacter calcoaceticus* (DiMarco, (1994), supra). In the presence of an inducer such as PHBA, association of pobR with its ligand fosters binding by RNA polymerase and leads to transcription of pobA. It is contemplated that an alternative approach to generating a PHBA-producing *P. mendocina* strain would involve the manipulation of the pobR genes controlling each respective pobA gene. For example, pobR genes could be genetically altered or disrupted so as to prevent transcription of all pobA genes, resulting in inhibited PHBH expression and accumulation of PHBA in the altered cells.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLES

General Methods

Procedures for the genetic manipulations of cellular genomes are well known in the art. Techniques suitable for use in the following examples may be found in Sambrook, J. et al., *Molecular Cloning: A Laboratory Manual*, Second Edition, Cold Spring Harbor Laboratory Press (1989).

Materials and methods suitable for the maintenance and growth of bacterial cultures are well known in the art. Techniques suitable for use in the following examples may be found in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994) or Thomas D. Brock in *Biotechnology: A Textbook of Industrial Microbiology*, Second Edition (1989) Sinauer Associates, Inc., Sunderland, Mass. All reagents and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "h" means hour(s), "min" means minute(s), "sec" means second(s), "d" means day(s), "mL" means milliliters, "L" means liters.

Cell strains:

The Pseudomonas strains KRC16 (ATCC 55886) and KRC50 were used for transformation and production of PHBA.

Growth Conditions

Typically, studies were conducted in flasks and 1 & 10-L fermenters and the fermentation modes used were batch, Fed-Batch and continuous. The medium most commonly used was a basal medium containing 0.48 g/L of yeast extract ("lean medium") or the same medium but with 4 g/L yeast extract and 10 g/L N-Z-amine E ("rich medium" Sheffield Products, Kraft Inc.), glucose was the carbon source and ammonia the inorganic nitrogen source.

Rich medium is available commercially from a variety of sources as from GIBCO/BRL (Gaithersburg, Md.) for example. Other media amenable to the procedures of the present invention are common in the art and are fully described in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994).

It is preferred that the cells are cultured in a 2-phase process, where the cells are first grown to a suitable cell density in rich medium in the first stage and then transferred to a production medium containing the aromatic substrate for PHBA production in a second stage. Preferred cell densities for the first and second stage culture are from about 0.1 g/L to about 50 g/L.

Analysis of Various Toluene Metabolites by Gas Chromatography

Compounds were prepared for GC analysis as follows: 10 mg of each compound was dissolved in 500 µL of ethylacetate and 500 µL of N,O-bis(trimethylsilyl) trifluoroacetamide (BSTFA). This mixture was heated for 30 min at approximately 80° C. to allow derivatization of the compounds. The reaction was then allowed to cool down to room temperature and the volume was adjusted to 1.0 mL as needed. A 1:10 dilution was performed with all compounds and 100 µL of each solution was dispersed into a GC vial. Samples were analyzed by injecting 1.0 µL (1000 ng) into the column. The GC conditions used for analysis were: Initial temp. 100° C. for 5 min; increased to 200° C. over 20 min at 5° C./min. The GC column used was HP-5 cross linked 5% Phenylmethyl siloxane (30 M×0.32 ID). Using these conditions, the following retention times (min) were obtained for various compounds tested: p-cresol, 4.27; 4-hydroxybenzaldehyde, 10.22; 4-hydroxybenzylalcohol, 14.05; 4-hydroxybenzoic acid (PHBA), 17.12; protocatechuic acid (PCA), 21.74.

Example 1

Cloning and Sequencing of pobA-1 Gene
Mutagensis of *P. mendocina* KR1

A colony of *P. mendocina* KR-1 (Amgen, Thousand Oaks, Calif.) was inoculated into about 3 mL LB medium and the culture shaken at 30° C. overnight. Cells were diluted by 100 to 500 fold with LB medium and plated on agar plates of LB medium. Plates were incubated at 30° C. for between 5 h to 10 h. The colonies were treated with UV (30 wt, distance: 60 inch) for about 2 to 2.5 h. Surviving cells (about 5%) were then incubated at 30° C. overnight and then plated on agar plates having minimal medium containing nitrogen source, minerals, and salts. 20 µL toluene as a sole carbon source was added and the cultures were incubated at 30° C. for at least two days. The largest colonies were scored on the basis of size and collected. These colonies were considered fast-growing variants of toluene-metabolizing KR-1.

One such variant was isolated and termed KRC50. KRC50 was again subjected to mutagenesis by U.V. light and a further isolation of variants was conducted. The second set of variants produced KRC16 (ATCC 55886), which also metabolized toluene and has a growth rate higher than either KR-1 or KRC50.

Isolation of a pobA hybridization probe

The pobA gene from *P. mendocina* was obtained by PCR for use as a hybridization probe in the isolation of pobA from KRC16 and KR-1.

The primers 5'-CARTTRCTNCAYAANGTNGGNAT-3' [SEQ ID NO:9] and 5'-CTAYTCNATYTCYTCRTANRG-3' [SEQ ID NO:10], based on the published sequence of the pobA gene from *P. fluorescens* [SEQ ID NO:5] (See, van Berkel, W. J. H. et al., supra) were used in a PCR reaction consisting of 100 μL reaction mixture which contained: 0.5 mM dNTPs, reaction buffer (final concentration of 10 mM Tris-HCl, pH 8.3, 50 mM KCl, 1.5 mM $MgCl_2$, and 0.01% gelatin), 0.1 μg of *P. mendocina* genomic DNA, 1 unit of Taq® DNA polymerase.

The DNA sample was denatured at 94° C. for 1 min, and annealed at 45° C. for 2 min. Polymerization was done at 72° C. for 3 min with an increased extention time of 5 sec per cycle. The polymerase chain reaction was accomplished by 30 cycles. The PCR DNA fragment was detected and analyzed by regular 1% agarose gel electrophoresis with ethldium bromide. A 1.2 kb PCR DNA fragment containing the pobA gene was isolated and cloned into the vector of PCRscript (Pharmacia Biotech, Piscataway, N.J.).

Preparation of genomic DNA from *P. mendocina* for isolation of pobA-1

50 mL of culture medium was used for the isolation of *P. mendocina* genomic DNA. The cells of an overnight culture were spun down at 6000 rpm, 4° C. for 10 min. Supernatant was decanted and the pellets were resuspended with 5 mL TEG (25 mM Tris-HCl, 10 mM EDTA, 50 mM glucose, pH 8). About 1.5 mL of RNAse (100 ug/mL) was added into the mixture. The sample was kept at room temperature for 5 min, and then extracted with phenol twice. The two phases were separated by a centrifugation at 6000 rpm for 10 min. The aqueous phase was extracted with phenol:chloroform twice. Two volumes of 100% ethanol was added to the aqueous phase to precipitate DNA. After 20 min the solution was centrifuged at 10,000 rpm, and the pellet was collected, dried, and resuspended in about 2 to 5 mL TE buffer (10 mM Tris-HCl, 1 mM EDTA, pH 7.6). The DNA samples were then dialyzed against TE buffer at 4° C. overnight.

Identification of pobA-1 gene from *P. mendocina* genomic DNA

10 μg of *P. mendocina* genomic DNA was used for Southern blot analysis using the pobA hybridization probe described above. DNA samples were first digested with EcoRI, HindIII and SphI and the digests were analyzed by 1% agarose gel electrophoresis. The DNA samples were then transferred to nitrocellulose membrane by denaturation and neutralization as described previously. The membranes were exposed to U.V. light for about 2 min to produce nucleic acid crosslinking. Prior to crosslinking the membrane had been prehybridized for about 1 to 2 h at 65° C. in a solution containing 5× SSC, 0.1% (w/v) SDS, 0.5% (w/v) blocking reagent (DuPont, Wilmington, Del.) and 5% (w/v) Dextran Sulfate.

For ease of identification the 1.2 kb DNA pobA probe was labeled with a fluorescenin nucleotide in a 30 μL reaction mixture containing: a random primer, reaction buffer, fluorescenin nucleotide mix and Klenow enzyme at 37° C. for 1 h. The labeled probe was then hybridized to the membrane-bound genomic DNA in the same buffer for 16 h at 65° C. After hybridization, the membrane was washed for 15 min in 2× SSC, 0.1% SDS, followed by a second 15 min wash in 0.2× SSC, 0.1% SDS at 65° C. The membrane was then blocked for 1 h in buffer containing 0.5% blocking reagent and then incubated with antifluoresein HRP conjugate (1:1000) at room temperature for 1 h.

After the incubation the membranes were washed four times for 5 min with 0.1 M Tris-HCl pH 7.5, 0.15 M NaCl, and incubated in a chemiluminescence reagent (Renaissance, nucleic acid chemiluminescent reagent, DuPont, Wilmington, DE) for 1 min at room temperature, and then exposed to the REFLECTION™ film (DuPont, Wilmington, Del.). In this manner portions of the genomic DNA hybridizing to the pobA probe were isolated.

Cloning the pobA-1 gene

A partial genomic DNA library of *P. mendocina* KR1 was prepared. Genomic DNA was restricted with SphI which produced fragments of about 3.0 kb. The fragments were recovered using the DNA preparation kit, GeneClean Bio 101 (Vista, Calif.). The SphI fragments were ligated into a SphI digested pUC18 vector (Pharmacia Biotech, Piscataway, N.J.) and the recombinant plasmids were used to transform Dh5-a *E. coli*. Analysis of the transformants by minipreparation and mini agarose gel electrophoresis (Sambrook, supra) indicated that about 80% of plasmid DNA contained an insert of about 3.0 Kb in length. Plasmids containing the 3.0 kb insert were termed pUC3.0k.

Confirmation and Isolation of pobA-1 with toluidine

The correct isolation of pobA-1 was confirmed using a colorometric assay essentially as described by Parke ("Application of p-Toluidine in Chromogenic Detection of Catechol and Protocatechuate, Diphenolic Intermediates in Catabolism of Aromatic Compounds", *Applied and Environmental Microbiology*, August 1992, 2694–2697).

Transformants containing the 3 kb insert were selected from the agar plates with ampicillin and were transferred onto the agar plates containing minimal medium, supplemented with 50 μg p-toluidine, 1 mM PHBA, 2.5 mM proline and 1 ug/mL thiamine and iron. The plates were incubated at 37° C. overnight.

Activity of pobA-1 and the production of protocachuate was confirmed by the appearance of a color on the plates.

Sequencing of the pobA-1 gene

The plasmid of pUC3.0k pobA was used for DNA sequencing. The DNA sequencing with synthetic primers was done at The Biopolymer Laboratory, Department of Microbiology and Immunology at the University of Maryland, School of Medicine according to standard methods. Accordingly the sequence of pobA-1 was determined and is given as SEQ ID NO: 1.

Example 2

Cloning of pobA-1 into a Suicide Vector and Transformation of *P. mendocina*

Cloning of the 3.0 kb pobA gene fragment into suicide vector pARO180

The 3.0 kb pobA gene fragment was isolated from pUC3.Ok by digesting the plasmid with SphI and further isolation by gel electrophoresis. The isolated 3.0 kb restriction fragment of pobA gene was then ligated with the SphI digested moblilizable suicide vector pARO180 (Parke, *Gene* (1990), 93(1), 135–7) to produce pARO3.0pobA. Plasmid pARO180pobAOmega contains an omega fragment inserted into the HindIII site of the first pobA gene on a 3.0 kb SphI DNA fragment.

Prior to ligation the HindIII site adjacent to the SphI site on pARO180 was destroyed using a Klenow fragment (FIG. 1(*a*)) pARO3.0pobA was then used to transform Dh5α *E. coli*.

Disruption of the pobA-1 gene with Omega element

A 2.0 kb HindIII restriction fragment of omega element (Prentki et al., Gene 29, 303, (1984), was inserted into the HindIII site of pARO3.0pobA which is located within the coding region of the pobA gene. The resulting plasmid was designed as pARpobA omega.

Introduction of the disrupted pobA gene into P. mendocina strain KRC16

Figure 2:
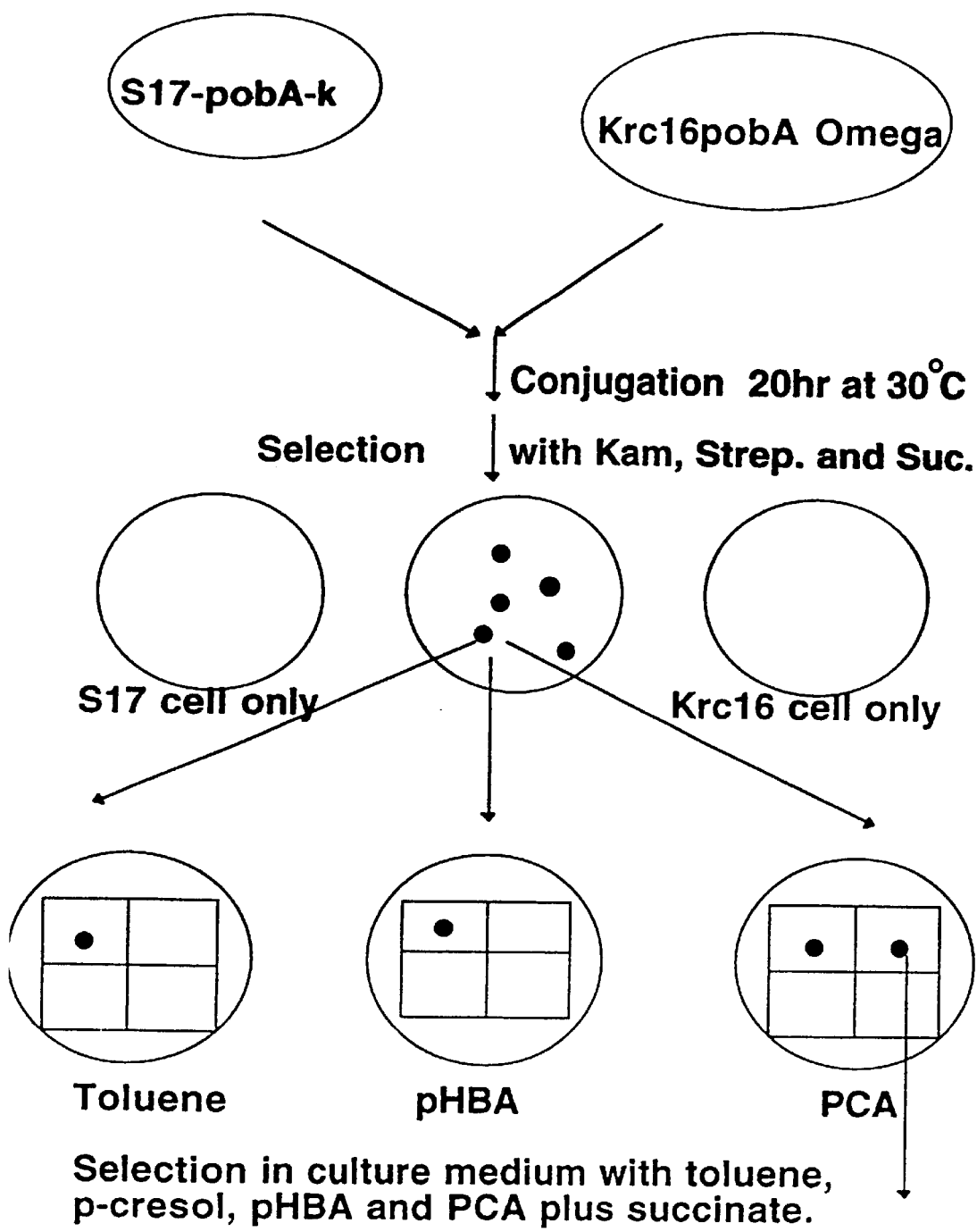
FIG. 2 is schematically represents the plasmid contructs needed for inactivation of pobA-1 and pobA-2.

The mobilizing E. coli strain S17-1 (Parke et al., supra) was used to introduce the disrupted pobA-1 gene containing the omega element into P. mendocina KR16 (FIG. 2).

pARpobA omega containing the 3.0 kb omega-disrupted pobA-1 was used to transform KRC16 using a standard transformation procedure as described below. A single colony of S17-1 strain having the plasmid of pobAomega was inoculated in 20 mL LB medium, and grown at 37° C. until log phase. Additionally untransformed P. mendocina strain KR16 was also inoculated in 20 mL LB medium and incubated at 30° C. until log phase. The cells of both strains were washed with LB medium two times and resuspended in LB medium. A mixture of donor and recipient cells [S17-1 cells and P. mendocina KR1 ] at a ratio of 1:4 was plated on the agar plates of LB medium. The plates were incubated at 30° C. for 8 h. The cells were collected and then plated on the agar plates containing phosphate buffer, 1 mM succinate, 10 mM streptomycin. The colonies of P. mendocina strain which can grow on the selection plates were scored and collected. Positive transformants were designated KRC16::pobAΩ (FIG. 2).

Identification of the disruption of pobA-1

Genomic DNA was isolated from wildtype and mutant KRC16::pobAΩ P. mendocina and restricted with SphI and then subjected to 1% agarose gel electrophoresis. After gel electrophoresis, the DNA samples were transferred to nylon membrane, and denatured and neutralized as described previously. The membranes were exposed to UV for about 2 min and the membrane was prehybridized for about 1 to 2 h at 65° C. in a solution containing 5× SSC, 0.1% (w/v) SDS, 0.5% (w/v) blocking reagent (DuPont, Wilmington, Del.) and 5% (w/v) Dextran Sulfate.

The 1.2 kb DNA fragment of pobA-1 (Example 1) was labeled with fluorescenin nucleotide in a 30 μL reaction mixture containing random primer, reaction buffer, fluorescenin nucleotide mix and Klenow enzyme at 37° C. for 1 h. Hybridization to labeled probe (16 h at 65° C.) was done by using the above-described solution.

After hybridization, the membrane was given one 15-min wash in 2× SSC, 0.1% SDS, and one 15-min wash in 0.2× SSC, 0.1% SDS (65° C.). The membrane was blocked for 1 h in buffer of 0.5% blocking reagent and then incubated with antifluoresein HRP conjugate (1:1000) at room temperature for 1 h. After the membrane was washed for 5-min. with buffer of 0.1 M Tris-HCl pH 7.5, 0.15 M NaCl, it was incubated in the chemiluminescence reagent for 1 min at room temperature, and then exposed to the REFLECTION™ film. Analysis of the exposed film confirmed the presence of the disrupted pobA-1, seen as a shift in the mobility from the 3.0 kb fragment of the wildtype.

Example 3

Analysis of PHBA Production in pobA-1(−) P. mendocina

Example 3 demonstrates the conversion of toluene to PHBA by P. mendocina strains KRC16::pobAΩ, and KRC16.

Organisms were initially grown on LB agar plates containing (gr): tryptone, 10.0; yeast extract, 5.0; sodium chloride, 10.0; agar Noble, 15.0; double distilled $H_2O$, 1.0 liter (pH ~6.6). Plates were incubated for ~60 h at 30° C. and were then stored at 4° C. One liter flasks (×20) each 125 mL center-well flask contained 25 mL of the PHBA medium containing (gr): sodium phosphate, monobasic, 1.85; potassium phosphate, dibasic, 5.84; ammonium sulfate, 1.50; glucose, 1.0; yeast extract, 0.25; tryptone, 0.25; double distilled water, 1.0 liter; (pH 7.0–7.2) and 250 μL of trace minerals. The trace minerals solution contained the following which were added to ~50 mL of double distilled $H_2O$ containing 1.0 mL of concentrated HCl, (in mg): $MgCl_2$, $6H_2O$, 2.50; $CaCl_2$, $2H_2O$, 1.00; $MnCl_2$, $4H_2O$, 400; $Na_2MoO_4$, $2H_2O$, 750; $FeSO_4$, $7H_2O$, 100; $CuSO_4$, $5H_2O$, 100; $ZnSO_4$, $7H_2O$, 100. The volume was adjusted to 100 mL. Trace mineral solution (1.0 mL) was added to 100 mL of the minimal medium after autoclaving. Toluene (500 μL) was added to the center-well. Cells were grown for 24 h. Culture suspensions (5 mL) were then used to inoculate 200 mL of the fresh medium in one liter flasks. These were incubated with shaking for an additional 24 h. Culture supernatant (50 mL) of each strain was acidified to pH 2–3 and extracted (×3) with ethylacetate (50 mL), dried over magnesium sulfate and evaporated to dryness under a stream of nitrogen. Samples were resuspended in ethylacetate (500 μL) and BSTFA (500 μL) was added. The vials were capped and heated to ~80° C. for 30 min to allow for complete derivatization. Samples were then transferred to GC vials and the volume was adjusted to 1.0 mL and were analyzed by GC as outlined above.

GC analysis showed the presence of PHBA in cultures of KRC16::pobAΩ cells grown on toluene. This sample was then submitted for GC/MS analysis for further confirmation of the presence of pHBA and PCA.

Example 4

Determination of the Presence of an Alternate pobA Gene

Conversion of PHBA to Protocatechuate by P. mendocina Strains KR16::pobAΩ and KR1 Following Growth on p-Cresol Since strain KR1::pobAΩ contains the interrupted pobA gene, this organism is expected to be incapable of converting PHBA to protocatechuate (PCA).

Organisms were grown on Laura Broth agar (LB) plates. Flasks (8×125 mL) each containing 25 mL of PHBA minimal medium were set up and p-Cresol (1 mM filter-sterilized). Flasks were inoculated with colonies from 1.5 plates per flask and were incubated at 30° C. on the shaker (200 RPM) for ~24 h. Cells obtained, (KR16pobAΩ, 6.26 g, and KR1, 6.37 g) were then stored at −80° C. until needed. The PEG buffer contained: 50 mM sodium phosphate buffer plus 10% glycerol, 1.0 mM DTT and 0.2 mM $MgCl_2$. Cells were then disrupted by passing twice through the French Pressure cell (⅜", 20,000 PSI). The cell debris was removed by centrifugation for 25 min at 38,000× g at 4° C. PMSF (phenylmethysulfonyl flouride) was added for a final concentration of 200 micro Molar after the cells were disrupted. The second pass through the French Pressure Cell was followed with a 3.0 mL rinse with PEG buffer. The protein concentration in the crude extract was determined using the Bicinchoninic acid (BCA) method as described by the manufacturer (Pierce, Rockford, Ill.).

The Effect of Buffers on the Rate of PHBA Hydroxylation

To study the effect of various buffers on the rate of PHBA hydroxylation, two separate buffers, Tris/HCl pH 8.0 and 50 mM sodium phosphate pH 6.8 buffers were used. The incubation mixtures for conversion of PHBA to PCA contained: NADPH, 6.0 μmoles; PHBA, 11.6 μmoles; FAD, 1.0 μmole and 2.0 mg protein of each extract (KR16::pobAΩ and KR1) and buffer to a total volume of 5 mL. After protein addition, the reaction mixtures were incubated with shaking at 30° C. for 5 min, stopped by the addition of 2 drops concentrated HCl, and extracted (×3) with diethyl ether (5 mL). The organic pool was dried over $Na_2SO_4$ and evaporated to dryness under a stream of nitrogen. The data is summarized below in Table 1.

TABLE 1

| Organism/Buffer | PCT formed μg/mL | PCA formed nmole/mL |
|---|---|---|
| KR16::pobAΩ Na-phosphate | 22 | 143 |
| KR1 Na-phosphate | 12.5 | 81 |
| KR1::pobAΩ Tris-HCl | 18.7 | 121 |
| KR1 Tris-HCl | 18.8 | 122 |

As can be seen by the data in Table 1, the PHBA hydroxylase is still active in KR16::pobAΩ because PCA is being formed from PHBA by this organism at levels comparable to the wild type (KR1) organism. No significant difference was observed in the amount of PCA formed with either phosphate or Tris buffer.

Conversion of PHBA to PCA by *P. mendocina* strains KRC16::pobAΩ KRC16, and KR1 when grown on p-Cresol Since strain KRC16::pobAΩ, KRC16, and KR1 contain the interrupted pobA gene, these organisms are expected to be incapable of converting PHBA to PCA.

Using a single loop of colonies from the agar plates, flasks containing p-cresol (1 mM), were inoculated and allowed to grow with shaking for 24 h at 30° C. These cultures were used to inoculate 200 mL of medium containing p-cresol (1.0 mM). Organisms were harvested after 24 h, washed, and the crude extract was obtained as described above.

Conversion of PHBA to PCA

Incubation mixtures contained: NADPH, 6.0 μmoles; PHBA, 11.6 μmoles; FAD, 1.2 μmoles; crude extract, 2.0 mg; Tris/HCl, pH 8.0 to final volume of 5.0 mL. Reaction mixtures were incubated for 5 min at 30° C. on shaker and were then stopped with 2 drops of concentrated HCl. The contents of the vials were extracted and prepared for GC analysis as explained above. Tests were performed in duplicates. Table 2 summarizes the data obtained.

TABLE 2

| Organism | PCA formed μg/mL | PCA formed μmoles/mL |
|---|---|---|
| KRC16::pobAΩ | 19.5 | 127 |
| KRC16 | 24.3 | 159 |
| KR1 | 21.6 | 141 |

As can be seen by Table 2, PHBA hydroxylase enzyme is active in all three organisms. KRC16::pobAΩ, in which the pobA gene was interrupted, is still capable of converting PHBA to PCA. This data implies the presence and functioning of more than one PHBA hydroxylase encoding gene (pobA) in *P. mendocina* KR1.

Effect of EDTA on PCA Accumulation in Cultures

The ability of *P. mendocina* strains KRC16::pobAΩ, KRC16, and KR1 to convert PHBA to PCA when grown on p-cresol was verified and the effect of ethylenediaminetetraacetic acid (EDTA) on the accumulation of PCA was studied. EDTA was expected to prevent further degradation of PCA and thus allow for its accumulation. Organisms were grown on p-Cresol (1.0 mM) and the crude extract was obtained as described before.

The reaction mixtures, which were set up in duplicates, contained: NADPH, 6.0 μmoles; PHBA, 11.6 μmoles; FAD, 1.2 μmoles; EDTA, 3.0 μmoles; protein, 2.0 mg; sodium phosphate buffer (50 mM) pH 6.8 to final volume of 5.0 mL.

Reaction mixtures were incubated for 5 min at 30° C. on the shaker and were terminated with 2 drops of concentrated HCl. Contents of the vials were extracted and prepared for GC analysis as before. Table 3 summarizes data for analysis.

TABLE 3

| Organism | PCA formed μg/mL | PCA formed μmoles/mL |
|---|---|---|
| KRC16::pobAΩ | 9.9 | 64 |
| KRC16::pobAΩ (-EDTA) | 9.3 | 61 |
| KRC16 | 19.9 | 78 |
| KR1 | 15.1 | 98 |

As can be seen in Table 3, PHBA hydroxylation is active in all organisms, and addition of EDTA resulted in about 5% increase in the amount of PCA formed.

Example 5

Cloning and Sequencng of pobA-2

Cloning of pobA-2 gene

A partial genomic DNA library of *P. mendocina* KRC16, was constructed as follows. Genomic DNA was restricted with SphI and 4.5 kp restriction fragments were isolated and recovered from an agarose gel using a DNA preparation kit, (GeneClean Bio 101, Vista, Calif.). Isolated DNA was then ligated into pUC18 at the appropirate SphI restriction sites and used to transform *E. coli* Dh5α.

Minipreparation and mini agarose gel electrophoresis indicated that about 80% of the transformants contained an insert of about 4.5 Kb in length.

Identification and isolation of pobA-2 by colony hybridization

The positive transformants were first grown on the LB agar plates overnight. The plates were chilled to 4° C. for one h. The colonies were then transferred onto the membrane discs. The membrane discs were treated with 0.5 N NaOH twice 2-min, and then washed twice for 2-min with 1 M Tris-HCl, pH 7.5. The DNA was fixed on the membrane by UV crosslinking. Membranes were prehybridized for about 1 to 2 h at 65° C. in a solution containing 5× SSC, 0.1% (w/v) SDS, 0.5% (w/v) blocking reagent (DuPont, Wilmington, DE) and 5% (w/v) Dextran Sulfate.

The 1.2 kb DNA fragment of pobA gene, constituting the pobA hybridization probe, was labeled and used to detect the presence of pobA-2 in essentially the same manner as it was used to confirm the presence of pobA-1 as described in Example 1.

The plasmid DNA was isolated from the positive colony detected with colony hybridization. The size of the insert was determined by the SphI digestion and miniagarose gel electrophoresis.

Sequencing of the pobA-2 gene

The plasmid of pUC4.5k pobA was used for DNA sequencing. The DNA sequencing with synthetic primers was done at The Biopolymer Laboratory, Department of Microbiology and Immunology at the University of Maryland, School of Medicine according to standard methods. Accordingly the sequence of pobA-2 was determined and is given as SEQ ID NO:2.

Figure 1B:
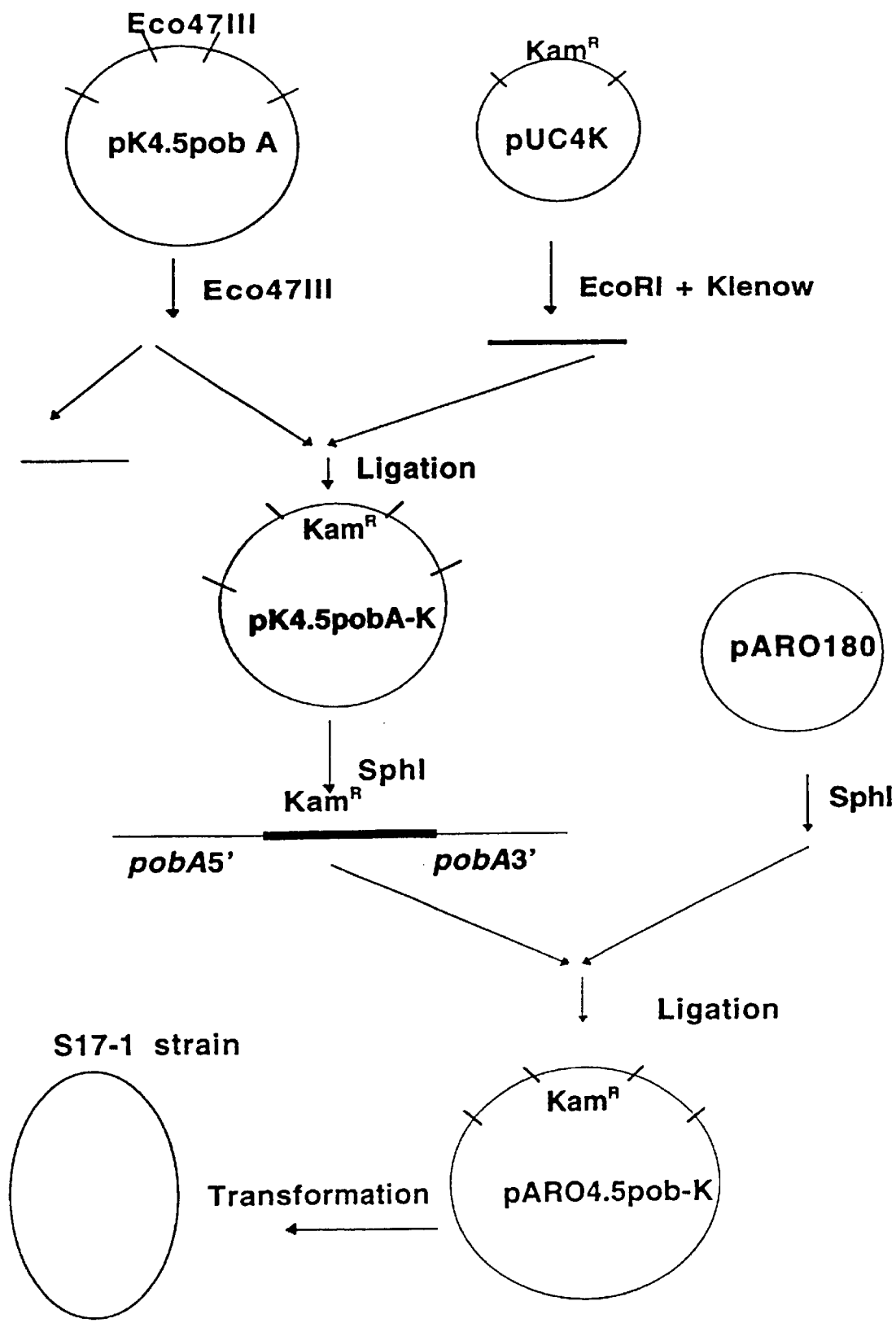

Example 6
Construction of the Disrupted pobA-2 and Cloning into a Suicide Vector Disruption of pobA-2 gene by deletion and insertion The Kam resistance gene cassette was removed from the plasmid pUC4K (Pharmacia Biotech, Piscataway, N.J.) by digesting with EcoRI (FIG. 1(b)). Sticky ends were then repaired with Klenow. pK4.5pobA, containing the 4.5 kb fragment encoding pobA was then digested with Eco47III, which resulted in a Eco47III fragment being deleted from the coding region of pobA-2 on the 4.5 kb SphI fragment (FIG. 1(b)).

The Kam resistance gene cassette was then inserted into the Eco47III digested pK4.5pobA plasmid to form the plasmid of pK4.5pobA-Kam. The orientation of the Kam gene cassette in the pobA gene was determined by the restriction mapping of the resulted plasmid.

Cloning of the disrupted pobA-2 gene into suicide vector

The disrupted pobA-2 gene with Kam gene cassette was digested with SphI and the resulting DNA fragment was ligated with the SphI digested pARO180 plasmid to produce pARO4.5pob-K, which was then used to transform S17-1 *E. coli* (FIG. 1(b)). Positive colonies were selected on the agar plates on the basis of Kam resistance.

Introduction of the disrupted pobA-2 gene into the mutant of *P. mendocina* KRC16::pobAΩ

A single colony of S17-1 strain having the plasmid of pARP4.5pobA-Kam (FIG. 1(b)) was inoculated in 20 mL LB medium, and grown at 37° C. to log phase. Another colony of KRC16::pobAΩ was inoculated in 20 mL LB medium and incubated at 30° C. and grown to log phase.

The cells of both cultures were washed twice with LB medium and resuspended in LB medium. S17-1 cells and *P. mendocina* KRC16::pobAΩ were mixed at a ratio of 1:4 and were plated on agar plates of LB medium. The plates were incubated at 30° C. for 8 h. The cells were collected and then plated on the agar plates containing phosphate buffer, 1 mM succinate, 10 mM streptomycin and 25 μg/mL Kanimycin, and Kam-resistant colonies were selected.

Selection *P. mendocina* having a disruption in both pobA-1 and pobA-2

A set of agar plates containing various substrates were used to select the mutants. The substrates were toluene, 20 μL for 30 mL medium, 1 mMp-cresol, 1 mM PHBA or 1 mM PCA respectively. The colonies were plated on these four plates containing different substrates as sole carbon source. Only the colonies of the mutants which cannot grow in the presence of PHBA and either toluene or p-cresol were scored while all of the colonies were grown with PCA. A similar experiment for further confirmation of the mutants was also conducted with liquid minimal medium containing the various substrates such as toluene (200 μL for 20 mL medium), 1 mM p-cresol, 1 mM PHBA or 1 mM PCA. The cell density was monitored with a spectrophotometer. The mutants which did not utilize toluene and PHBA in the liquid minimal medium were identified as the *P. mendocina* strain having a disruption of both pobA-1 and pobA-2 genes.

Identification of the disruption of pobA-1 and pobA-2 genes the pobA(−) *P. mendocina* strain Genomic DNA was isolated from the mutant strain of KRC1651 (ATCC 55885). DNA from both wild type and mutant cells were digested with SPhI and then subjected to 1% agarose gel electrophoresis. After gel -electrophoresis, the DNA samples were transferred to nylon membrane, and denatured and neutralized as described previously. The membranes was exposed to the UV for about 2 min for UV crosslinking of nucleic acids. Membranes were prehybridized for about 1 to 2 h at 65° C. in a solution containing 5× SSC, 0. 1% (w/v) SDS, 0.5% (w/v) blocking reagent (DuPont, Wilmington, Del.) and 5% (w/v) Dextran Sulfate. The 1.2 kb DNA fragment of pobA gene was labeled with fluorescenin nucleotide in a 30 μl reaction mixture containing random primer, reaction buffer, fluorescenin nucleotide mix and Klenow enzyme at 37° C. for 1 h. Hybridization to labeled probe (16 h at 65° C.) was done by using the above-described solution. After hybridization, membrane was giveN one 15-min wash in 2× SSC, 0.1% SDS, and one 15-min wash in 0.2× SSC, 0.1% SDS (65° C.). The membrane was blocked for 1 h in buffer of 0.5% blocking reagent and then incubated with antifluresein HRP conjugate (1:1000) at room temperature for 1 h. After the membrane was washed four 5-min with buffer of 0.1 M Tris-HCL pH 7.5, 0.15 M NaCl, it was incubated in the chemiluminescence reagent for I min at room temperature, and then exposed to the REFLECTION™ film.

Example 7

Production of PHBA with pobA(−) *P. mendocina*

Conversion of Toluene to PHBA by the poba(−) mutants *P. mendocina* Strains KRC1615 KRC1616 and KRC1651

Example 7 was designed to determine the ability of *P. mendocina* KRC1615, KRC1616 and KRC1651 pobA(−) mutants to convert toluene to pHBA when grown on succinate. The PHBA minimal medium with the following changes was used throughout the experiment: toluene, glucose, and tryptone were omitted and sodium succinate (at 1% final conc.) and yeast extract (at 0.01% final conc.) were added (pH 7.1). Cells were harvested and washed after 21 h of growth. Center-well flasks were set up with the following additions: medium, 22.0 mL; trace mineral, 250 μL; toluene, 750 μL (center-well only); organisms, 300 mg (wet weight). Flasks were incubated with shaking at 30° C. Samples were prepared for GC analysis as before. GC/MS analysis was performed and results are attached as FIG. 5.

Figure 5:
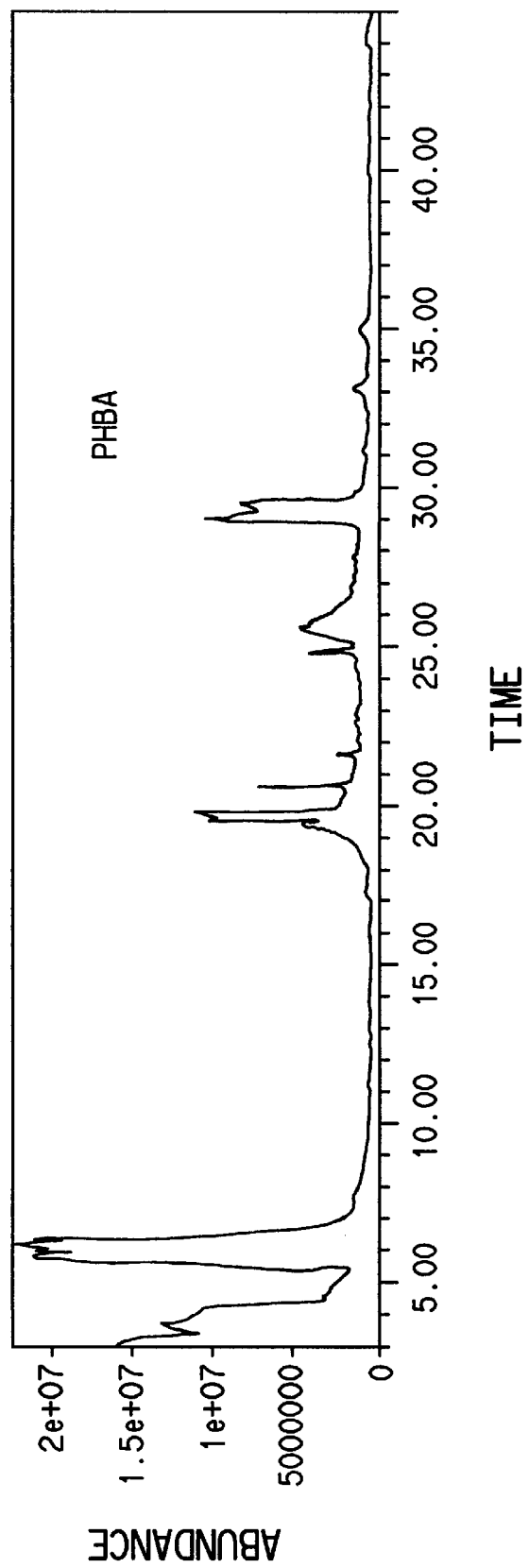
FIG. 5 is a GC/MS analysis of PHBA production (PHBA peak indicated) from P. mendocina strains containing disrupted pobA-1 and pobA-2 genes.

As can be seen in FIG. 5, no PCA was detected in any samples. PHBA was detected in some incubations after 50 h (strains KRC1615, KRC1616 and KRC1651) and after 95 h (KRC1616) as indicated below in Table 4:

TABLE 4

| Strain | Time (h) | μg PHBA formed |
| --- | --- | --- |
| KRC1615 | 50 | 39.5 |
| KRC1651 | 50 | 770 |
| KRC1651* | 50 | 4500 |
| KRC1616 | 95 | 39.8 |
| KRC1616* | 95 | 58.8 |

*Indicates duplicates

As demonstrated by the data in Table 4 strain KRC1651 was most active in PHBA production.

These data indicate that strain KRC1651 is capable of converting toluene to PHBA and accumulating it. This implies that the pathway to form PCA from PHBA has been blocked in this organism. Further experiments on PHBA accumulation were therefore planned using *P. mendocina* KRC1651.

Effect of Glucose, Succinate and $MgCl_2$ on Growth and PHBA Production by the pobA(−) mutant KRC1651

The center-well flasks containing 200 mL of Luria Broth (LB) medium: Tryptone (1%); yeast extract (0.5%); sodium chloride (1%); double distilled water up to 1.01. One mL of a filter sterilized solution of kanamycin (4.0 mg/l mL) was added to each flask after cooling. Flasks were inoculated with KRC1651 and incubated with shaking at 30° C. After 24 h, 1.0 mL of toluene was added to the center-well and incubation was continued for one more h. Organisms were harvested and the pellets were washed 2× with phosphate buffer (pH 7.0). Final centrifugation at 17,000× g for 30 min resulted in 4.34 g wet weight of cells.

Center-well flasks containing the PHBA minimal medium in which yeast extract was replaced with 1.0 mM of glucose or 1.0 mM of sodium succinate were inoculated with 620 mg (wet weight) of cells. Varying concentrations of $MgCl_2$ (1.2 mM–5.0 mM) were used in these experiments. Toluene (2.0 mL, center-well) was added and the flasks were incubated with shaking at 30° C. Flasks with standard PHBA trace mineral solutions were sampled at 2, 5, 24, 48 and 68 h. Flasks with increased $MgCl_2$ concentration were sampled at 2, 48 and 68 h. These were extracted, derivatized and analyzed as described above. The results of these analysis are summarized below in Tables 5 and 6.

TABLE 5

| Glucose Medium Sample | PHBA formed/mL | Sample | PHBA formed/mL |
|---|---|---|---|
| Standard-2 | 13.8 μg | Increased $MgCl_2$-2 | 11.6 μg |
| Increased $MgCl_2$ | 24.16 μg | Increased $MgCl_2$-48 | 0.08 mg |
| Standard-24 | 0.11 mg | Increased $MgCl_2$-68 | — |
| Standard-48 | 0.44 mg | | |
| Standard-68 | 0.04 mg | | |

TABLE 6

| Succinate Medium Sample | PHBA formed | Sample | PHBA formed |
|---|---|---|---|
| Standard-2 | 32.5 μg | Increased $MgCl_2$-2 | 9.8 μg |
| Increased $MgCl_2$ | 38.8 μg | Increased $MgCl_2$-48 | 26.4 μg |
| Standard-24 | 0.07 mg | Increased $MgCl_2$-68 | 22.48 μg |
| Standard-48 | 35.9 μg | | |
| Standard-68 | 33.64 μg | | |

As can be seen by the data, PHBA concentrations decreased after 24 h, however no PCA was detected in samples. Further, the higher concentrations of $MgCl_2$ did not increase the ability of organisms to transform toluene to PHBA.

Conversion of PHBA to PCA by Crude Extracts of KRC1651 and KRC16

Purpose: to determine the ability of *P. mendocina* strains KRC1651 (ATCC 55885) and KRC16 to convert PHBA to PCA. The cells obtained above were disrupted as described before and the crude extract obtained was used for experiments described above. The reaction mixture contained: NADPH, 6.0 [moles; PHBA, 11.6 μmoles; FAD, 1.2 μmoles; EDTA, 3.0 μmoles; protein, 2.0 mg; sodium phosphate buffer (50 mM) to final volume of 2.0 mL. To insure that the PCA formed was not further degraded, ethylenediaminetetraacetic acid (EDTA) was used as an inhibitor of protocatechuate dioxygenase. The reaction mixture was incubated with shaking for 30 min at 30° C. after which it was terminated by acidifying to <pH 2 followed by addition of 10 mL ethylacetate. This mixture was then allowed to remain at room temperature for approximately 16 h. It was then further extracted (×2) using 5 mL of ethylacetate. The organic layer was dried over $Na_2SO_4$ and then evaporated to dryness under a stream of nitrogen. Samples were prepared for GC analysis as before and results are summarized below in Table 7:

TABLE 7

| Sample | PHBA Detected | PCA Formed per Reaction |
|---|---|---|
| KRC1651 | 0.88 mg | — |
| KRC-16 | 0.86 mg | 3.9 μg |

As can be seen by the data, no PCA was detected by GC analysis of the pobA(−) strain *P. mendocina* KRC1651 (ATCC 55885). Further, the strain containing the pobA gene (*P. mendocina* KRC16) showed formation of 3.9 μg of PCA indicating that it is converting PHBA to PCA.

Example 8

Effect of Glucose Concentration on PHBA Production

Example 8 demonstrates the effect of glucose on cell yield and the production of PHBA from KRC1651 (ATCC 55885).

Cell Yield—Fed Batch

Cell yield was tested in the mineral medium with 2 g/L glucose and 0.48 g/L yeast extract. The cell yield obtained was corrected for yeast extract contribution and was the highest on fructose and the lowest on succinate, >0.38 and >0.22 gr cell/gr substrate, respectively. Yeast extract, peptone, casamino acids, tryptone, N-Z-amine E, corn steep liquor, and soytone were tested as organic nitrogen additives to the similar medium. All additives stimulated growth and cell yield. The growth rate was influenced by temperature, medium additions and the density of the culture. The initial growth rates at low cell densities were maximal at 34–36° C. with doubling times of 35 and 33 min. respectively. At higher cell densities, the growth rate was much slower and was estimated in fermenters, at 10 gr cells/L to have a doubling time of about two hours. The final cell densities on lean medium were limited to <4.7 g/L, Fed-Batch studies with addition of glucose, ammonia, yeast extract and N-Z-amine E achieved 40.0 g/L. Cell yield based on glucose ranged from 0.22 to 0.47 g/g in the lean medium to 0.41 to 0.60 in the rich medium.

Cell Yield—Continuous Culture

Using glucose as a carbon source, *P. mendocina* demonstrated an ability to grow in continuous culture. Cultures were prepared with 1-L SixFour fermenter with mineral medium, 10 g/L glucose, 0.75 g/L (NH4)2SO4 and 0.28 g/L yeast extract and at dilution rates ranging from 0 to 0.3 h (2.5 h doubling time). The cell yield in these cultures was 0.3 g/g.

Production of PHBA in Continuous Culture

The specific productivity of PHBA was tested at 1.25 to 4 g/L cell concentrations and 4 h incubation. Maximal productivity occurred at 0.125–0.5 g/L and it progressively decreased at 1 and 2 g/L.

Example 9

Effect of pH on PHBA Production

The effect of pH was determined on KRC1651 (ATCC 55885) grown in both rich and lean medium according to the conditions recited in the GENERAL METHODS.

pH had a significant effect on PHBA production, where increasing the pH from 6.3 to 7.4 increased PHBA specific productivity by about two fold. At higher pH values the specific productivity of PHBA varied with the medium used. Lean medium produced no change in PHBA specific productivity in a pH range of 7.2 to 7.9, while in rich medium the specific productivity increased by about 4 fold. The pH of the cultures should be maintained within a range of about from 6.3 to 7.4, where a range from about 7.2 to 7.7 is most preferred.

Example 10

Effect of Toluene and PHBA Concentration on the Production of PHBA

Example 10 demonstrates the effect of toluene concentration on the production of PHBA from KRC1651 (ATCC 55885). Two separate protocols were used for the analysis, one in 125 ml Culture flasks and the other under conditions of batch fermentation in a continuous feed bioreactor.
Culture Flasks Growth studies using KRC1651 (ATCC 55885) were performed in 125 mL sealed flasks with 5 mL minimal medium plus 0.28 g/L yeast extract and 10 g/L glucose. The flasks were incubated at 30° C. in incubator shaker. Growth was observed after 24 and 48 h visually or by OD measurement at 600 nm.

Mutants with higher tolerance to toluene and PHBA were selected by repeated transfers in media with increasing concentrations of toluene and PHBA. Repeated transfers produced strains that could grow on agar plates at 40 g/L PHBA and about 100 ppm toluene.

Both toluene and PHBA have a bacteriostatic and bacteriocitic effects. The growth of KRC1651 was significantly inhibited at about 100 ppm toluene or 10 g/L PHBA. Together these agents had an additive toxic effect.
Bioreactor KRC1651 (ATCC 55885) was used in bioreactor studies and grown in rich and lean medium. Production of PHBA from toluene can be enhanced by a continuous feed of toluene to a bioreactor to keep the steady state concentration of toluene in the reactor below toluene explosivity limits. The lower explosivity limits (LEL) for toluene is 120 ppm in the liquid phase, 1.2% v/v in the gas phase. Glucose was fed as a co-substrate for cell maintenance simultaneously with toluene feed. The standard system used consisted of 1 mM glucose, 60 ppm toluene, 0.25–0.5 g cells/L, and the incubation was for 3–4 h. The pH was controlled at 7.2 with addition of buffer. The effect of toluene concentration on PHBA production was examined at 30, 60, and 100 ppm.

The time course of PHBA production was followed from 0 to 24 h. PHBA production (based on accumulation) demonstrated a lag of 1 to 2 h where maximal productivity was at about 2–3 h. At later times a decline from 4 to 6–10 h and zero production from 6–10 h to 24 h was seen. No decline in PHBA concentration was observed. Results were comparable between rich and lean medium; however, in the rich medium the PHBA productivity was somewhat higher reaching a maximum of 60 ppm.

Example 11

Production of PHBA with pobA(−) P. mendocina— Effect of Mg+ on Toluene Tolerance Toluene and PHBA are known to incorporate and interfere with the integrity of bacterial membranes and function. Growth studies in the presence of inhibitory concentrations of toluene and PHBA were used to assess the protective effect of Mg ions.

Experimental: Growth studies using KRC1651 (ATCC 55885) were performed in 125 mL sealed flasks with 5 mL minimal medium plus 0.28 g/L yeast extract and 10 g/L glucose. The flasks were incubated at 30° C. in incubator shaker. Growth was observed after 24 and 48 h visually or by OD measurement at 600 nm.

Results: Magnesium ions increased KRC1651 tolerance to toluene and PHBA. Increasing Mg concentration from 2 to 12 mM enhances growth rate at 100 and 150 ppm toluene and allows growth at 100 ppm toluene and 5 g/L PHBA.

Example 12

Maximal Production Rates of PHBA

KRC1651 (ATCC 55885) was cultured in rich medium where the growth conditions of pH, glucose, Mg ion concentration and toluene were optimized for maximal PHBA production as described in Examples 8–11. With all conditions optimized, PHBA production varied with the method of production. The most apparent difference was between cells that grew in fermenters and flasks. Cells that grew in fermenters had an average specific productivity of 0.35 g/g-h and cells that grew in flasks had an average specific productivity of 0.11 g/g-h. The maximal specific productivity in fermenters occurs at 1–3 h and is estimated to be 1 g/g-h.

Example 13

Fed-Batch Fermentation of Toluene to PHBA

A two-step fermentation was carried out to demonstrate the production of PHBA from toluene using the P. mendocina KRC16KDpobA51 strain. This strain had disrupted pobA-1 and pobA-2 genes. The fermentation was carried out in two steps:

1. biomass built-up step (batch process), and
2. biotransformation step (fed-batch process)

During the first step, the P. mendocina KRC16KDpobA51 strain grew to high cell densities in a 5 L fermenter with approximately a 3 L working volume. The medium contained 1.2 g $KH_2PO_4$, 6 g $(NH_4)2SO_4$, 0.3 g $MgSO_4.7H_2O$, 20 mL/L trace elements, 20 g/L glucose, 20 g/L corn steep liquor, 1 mL/L polypropylene glycol and 1 g/L yeast extract. The trace elements contained 10 g/L citric acid, 1.5 g/L $CaCl_2.2H_2O$, 2.8 g/L $FeSO_4.7H_2O$, 0.39 g/L $ZnSO_4.7H_2O$, 0.38 g/L $CuSO_4.5H_2O$, 0.2 g/L $CoCl_2.6H_2O$, and 0.3 g/L $MnCl_2.4H_2O$. The phosphate, ammonia, Mg salts and trace elements were sterilized together and then titrated to pH 7.2 with KOH or $H_2SO_4$ before addition of the remaining components.

The second step commenced as a toluene fed-batch fermentation using glucose as co-feed at a rate of 3 g/h. The rate was decreased if glucose concentration rose above 1 g/L. Toluene was supplied at a rate that kept its concentration in the medium at 10–100 ppm. The initial cell density was 16.2 OD units. Over 18.5 h, a total of 67.3 g (0.73 moles) of toluene was fed during step 2 of the biotransformation. All of the toluene was not utilized and some was lost with the air exit-stream of the fermenter. After 18.5 h, a total of 38.1 g PHBA (0.278 moles) was produced. Table 8 summarizes the production of PHBA over time.

TABLE 8

| Time (h) | PHBA (g/L) |
|---|---|
| 0.0 | 0.0 |
| 1.0 | 0.0 |
| 1.4 | 0.0 |
| 2.4 | 0.7 |
| 3.4 | 1.7 |
| 4.5 | 3.4 |
| 5.4 | 6.1 |
| 6.4 | 7.6 |
| 7.3 | 6.9 |
| 8.3 | 10.7 |

TABLE 8-continued

| Time (h) | PHBA (g/L) |
|---|---|
| 9.3 | 9.1 |
| 10.5 | 8.9 |
| 11.5 | 9.1 |
| 12.7 | 10.7 |
| 14.5 | 9.7 |
| 15.5 | 12.1 |
| 17.0 | 11.4 |
| 17.4 | 12.6 |
| 18.5 | 12.6 |
| 18.5 | 12.7 |

What is claimed is:

1. A method for the production of p-hydroxybenzoate comprising:
   (i) culturing a pobA(−) Pseudomonas strain in a medium containing an aromatic organic substrate, at least one suitable carbon source, and a nitrogen source, wherein the pobA(−) Pseudomonas strain comprises pobA genes encoding the toluene monooxygenase toluene degradation pathway and wherein the pobA(−) Pseudomonas strain does not produce any detectable para-hydroxybenzoate hydroxylase, whereby p-hydroxybenzoate accumulates; and
   (ii) recovering the p-hydroxybenzoate.

2. The method of claim 1 wherein the genes encoding the toluene monooxygenase toluene degradation pathway of the pobA(−) Pseudomonas strain are characterized by a disruption in at least two pobA genes.

3. The method of claim 1 wherein the pobA(−) Pseudomonas strain is KRC1651 (ATCC 55885).

4. The method of claim 2 wherein at least one pobA gene encodes a para-hydroxybenzoate hydroxylase enzyme having a first amino acid sequence as set out in SEQ ID NO:4 or a second amino acid sequence as set out in SEQ ID NO:5.

5. The method of claim 2 wherein at least one pobA gene is pobA-1 and is defined by SEQ ID NO:1.

6. The method of claim 2 wherein at least one pobA gene is pobA-2 and is defined by SEQ ID NO:3.

7. The method of claim 1 wherein the aromatic organic substrate is selected from the group consisting of toluene, p-cresol, p-hydroxybenzyl alcohol, benzoate and p-hydroxybenzaldehyde.

8. The method of claim 7 wherein toluene is present in the medium in a concentration of less than 500 ppm.

9. The method of claim 7 wherein toluene is present in the medium from about 30 ppm to about 60 ppm.

10. The method of claim 1 wherein the suitable carbon source is succinate, lactate, acetate, ethanol, monosaccharides, oligosaccharides, polysaccharides, or mixtures thereof.

11. The method of claim 10 wherein the suitable carbon source is glucose or succinate.

12. The method of claim 1 wherein p-hydroxybenzoate accumulates at a concentration of at least 1 mM.

13. The method of claim 1 wherein p-hydroxybenzoate accumulates at a rate of about 0.01 g p-hydroxybenzoate/g-cells-h to about 1 g p-hydroxybenzoate/g-cells-h.

14. The method of claim 1 wherein the pobA(−) Pseudomonas strain is cultured at a pH of from about 6.3 to about 7.9.

15. The method of claim 1, the medium further containing $Mg^{+2}$ at a concentration of about 2 mM to about 12 mM.

16. A pobA gene encoding a para-hydroxybenzoate hydroxylase enzyme having the amino acid sequence as shown by SEQ ID NO:4 or SEQ ID NO:5.

17. The gene of claim 16 wherein the gene is pobA-1 and is defined by SEQ ID NO:1 or is pobA-2 and is defined by SEQ ID NO:3.

18. A transformed pobA(−) Pseudomonas strain comprising an amino acid disruption in at least two pobA genes.

19. The transformed pobA(−) Pseudomonas strain KRC1651 (ATCC 55885), KRC1616, and KRC1615.

20. A Pseudomonas strain selected from the group consisting of biological deposits identified as KRC1651 (ATCC 55885) and KRC16 (ATCC 55886).

21. A toluene monooxygenase *P. mendocina* variant having a cell density at least 6 fold greater than the wildtype under growth conditions of approximately 160 ppm toluene, the toluene monooxygenase *P. mendocina* variant produced by mutagenesis of the wildtype KR-1.

22. The toluene monooxygenase *P. mendocina* variant KRC16.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 1140 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
ATGAATACTC AAGTTGCTAT CATCGGCGCC GGTCCTTCGG GGCTTCTGCT CGGCCAACTG      60
CTGCACAAGG CCGGTATCGA AACCATCATC CTCGAGCGGC AGACTCCCGA CTATGTGCTC     120
GGCCGTATCC GGGCCGGCGT GCTGGAGCAG GGCACCGTCG ATATGTTGCG CGAAGCCGGT     180
GTTGCGCAAC GTATGGATGC CGAGGGGCTG GTCCATGAGG GGGTCGAGCT GGTGTTCGAC     240
GGCAAGCGCG TGCCGATTCA TCTGAAGGCA TTGACCGGCG GCAAGACCGT GATGGTTTAT     300
GGCCAGACTG AAGTCACCCG TGACCTGATG GATGCCCGCG TCGCTGTCGG CGCGCCCATC     360
GTGTACTCCG CCGAGAACGT GCAGCTGCAC GAACTCAAGG CGGCAAGCC  TTACGTCACC     420
TTCGAGAAGG ATGGCCAATC CCATCGCATC GATTGCGACT ACATCGCCGG TTGCGATGGC     480
TTCCATGGCA TCGCGCGCAA GAGCATTCCG GCCGGTGTCC TGACCGAGTA CGAGCGTGTC     540
TACCCGTTCG GCTGGCTGGG CCTGTTGTCA GACACCCCGC CGGTCCACGA GGAACTGATC     600
TACGCCCACC ACGAGCGCGG TTTCGTGCTG TGCAGCCAGC GTTCGCTGAC CCGCAGTCGC     660
TATTACTTGC AGGTTCCGCT GACCGACAAA GTCGAAGACT GGTCCGATGA GCGTTTCTGG     720
AACGAGCTCA AGGCCCGTCT TCCGCAGGAC GTGGCGGACA GGCTGGTCAC CGGCCCGTCC     780
CTGGAAAAGA GTATCGCCCC GCTGCGAAGC TTCGTGGTCG AACCGATGCA GTACGGCAAC     840
CTGTTCCTAG TGGGGACGC  CGCCCATATC GTGCCGCCGA CGGGGGCCAA GGGCCTAAAC     900
CTGGCCGCCT CCGACGTATG CTACCTGTAT CGAATCCTGA TCAAGGTCTA CAAGGAAGGT     960
```

```
CGCACCGACC TGCTGGAGAA GTATTCGGAG CTGGCTCTAC GCCGCGTGTG GAAAGGTGAA      1020

CGCTTCAGCT GGTTCATGAC CAATCTGCTG CACGACTTCG ACGGTCACCA GGACGCCTGG      1080

GATCAGAAGA TGCAGAAAGC CGACCGCGAG TACTACCTGA AGTCCCACGC TGGTCTGGCC      1140
```

(2) INFORMATION FOR SEQ ID NO:2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:2:
```
         GRNATRCTYC TYTANCTYAT C                                          21
```

(2) INFORMATION FOR SEQ ID NO:3:

(i) SEQUENCE CHARACTERISTICS:
        (A) LENGTH: 1188 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
ATGAAAACCC AGGTTGCCAT TATCGGTGCC GGTCCGTCCG GCCTGCTGCT CGGTCAATTG        60

CTGCACAAGG CGGGTATCGA CACCCTCATC GTCGAGCGCC AGACCCCTGA GTACGTGCTC       120

GGCCGCATCC GCGCCGGCGT GCTGGAACAG GGCACCGTGG ACATGCTCCG CGAGGCGGGC       180

GTGAGCGAGC GCATGGACGC CGAGGGCCTG GTACACCACG GCGTCGAGCT GGTGTTCGAT       240

GGCAAGCGGG TGCCGGTCCA CCTTACCGAG CTGACCGGTG GCAAGAGCGT GATGGTCTAT       300

GGCCAGACCG AAGTCACCCG CGACCTGATG GACGCCGGG CCGCCAGCGG CGCCCCCATC        360

GTCTACTCCG CCAGCAACGT GGAGCTGCAT GAACTCAAGG GCGAGCGCCC CTACGTGACC       420

TTCGAGAAGG ACGGCGAGCG GGTGCGCGTC GACTGCGACT ACATCGCCGG TTGCGACGGC       480

TTCCATGGCG TGTCGCGCAA GAGCATCCCG GAAGGCGTGC TGACCGAGTA CGAGCGCGTC       540

TATCCCTTCG GCTGGCTGGG CCTGCTCTCC GACACCCCGC CGGTGCATGA GGAACTCATC       600

TACGCCCACC ACGAGCGCGG CTTCTCCCTG TGCAGCCAGC GTTCCCTCAC CCGCAGCCGC       660

TACTACTTGC AGGTGCCGCT GACCGACAAG GTGGAGGACT GGTCCGACGA GCGCTTCTGG       720

AACGAGCTGA AGGCGCGTCT GCCCGAGGAC GTGGCGGCCA AGCTGGTGAC CGGCCCGTCC       780

CTGGAGAAGA GCATCGCGCC CCTGCGCAGC TTCGTGGTCG AGCCCATGCA GTACGGCCAT       840

CTGTTCCTGG TGGGTGATGC CGCCCACATC GTGCCGCCCA CCGGCGCCAA GGGCCTGAAC       900

CTGGCGGCTT CCGACGTCTG CTACCTCTAT CGCATCCTGG TGAAGGTGTA CCGCGAAGGC       960

CGTACCGACC TGCTGGAGAA ATACTCCGAA CTGGCCCTGC GCCGGGTGTG GAAAGGCGAG      1020

CGCTTCAGCT GGTTCATGAC CAACCTGCTG CACGACTTCG ACGGCCACAA GGACGCCTGG      1080

GACCAGAAGA TGCAGCAGGC CGACCGCGAG TACTTCCTCG GTTCCCACGC GGGCCTCGTG      1140

AACATCGCCG AGAACTACGT GGGCCTGCCC TACGAAGACG TGAAATAA                   1188
```

(2) INFORMATION FOR SEQ ID NO:4:

(i) SEQUENCE CHARACTERISTICS:
        (A) LENGTH: 268 amino acids
        (B) TYPE: amino acid

```
        (C) STRANDEDNESS: Not Relevant
        (D) TOPOLOGY: Not Relevant (ii) MOLECULE TYPE:  protein (xi) SEQUENCE DESCRIPTION: SEQ ID NO:4:

Met Asn Thr Gln Val Ala Ile Ile Gly Ala Gly Pro Ser Gly Leu Leu
 1               5                  10                  15

Leu Gly Gln Leu Leu His Lys Ala Gly Ile Glu Thr Ile Ile Leu Glu
                20                  25                  30

Arg Gln Thr Pro Asp Tyr Val Leu Gly Arg Ile Arg Ala Gly Val Leu
            35                  40                  45

Glu Gln Gly Thr Val Asp Met Leu Arg Glu Ala Gly Val Ala Gln Arg
        50                  55                  60

Met Asp Ala Glu Gly Leu Val His Glu Gly Val Glu Leu Val Phe Asp
65                  70                  75                  80

Gly Lys Arg Val Pro Ile His Leu Lys Ala Leu Thr Xaa Xaa Xaa Xaa
                85                  90                  95

Xaa Xaa Gly Gly Lys Thr Val Met Val Tyr Gly Gln Thr Glu Val Thr
            100                 105                 110

Arg Asp Leu Met Asp Ala Arg Val Ala Val Gly Ala Pro Ile Val Tyr
        115                 120                 125

Ser Ala Glu Asn Val Gln Leu His Glu Leu Lys Gly Gly Lys Pro Tyr
    130                 135                 140

Val Thr Phe Glu Lys Asp Gly Gln Ser His Arg Ile Asp Cys Asp Tyr
145                 150                 155                 160

Ile Ala Gly Cys Asp Gly Phe His Gly Ile Ala Arg Lys Ser Ile Pro
                165                 170                 175

Ala Gly Val Leu Thr Glu Tyr Glu Arg Val Tyr Pro Phe Gly Trp Leu
            180                 185                 190

Gly Leu Leu Ser Asp Thr Pro Pro Val His Glu Glu Leu Ile Tyr Ala
        195                 200                 205

His His Glu Arg Gly Phe Val Leu Cys Ser Gln Arg Ser Leu Thr Arg
    210                 215                 220

Ser Arg Tyr Tyr Leu Gln Val Pro Leu Thr Asp Lys Val Glu Asp Trp
225                 230                 235                 240

Ser Asp Glu Arg Phe Trp Asn Glu Leu Lys Ala Arg Leu Pro Gln Asp
                245                 250                 255

Val Ala Asp Arg Leu Val Thr Gly Pro Ser Leu Glu
            260                 265

(2) INFORMATION FOR SEQ ID NO:5:

(i) SEQUENCE CHARACTERISTICS:
        (A) LENGTH:  395 amino acids
        (B) TYPE:  amino acid
        (C) STRANDEDNESS: Not Relevant
        (D) TOPOLOGY: Not Relevant (ii) MOLECULE TYPE:  protein (xi) SEQUENCE DESCRIPTION: SEQ ID NO:5:

Met Lys Thr Gln Val Ala Ile Ile Gly Ala Gly Pro Ser Gly Leu Leu
 1               5                  10                  15

Leu Gly Gln Leu Leu His Lys Ala Gly Ile Asp Thr Leu Ile Val Glu
                20                  25                  30

Arg Gln Thr Pro Glu Tyr Val Leu Gly Arg Ile Arg Ala Gly Val Leu
            35                  40                  45
```

```
Glu Gln Gly Thr Val Asp Met Leu Arg Glu Ala Gly Val Ser Glu Arg
     50                  55                  60

Met Asp Ala Glu Gly Leu Val His His Gly Val Glu Leu Val Phe Asp
 65                  70                  75                  80

Gly Lys Arg Val Pro Val His Leu Thr Glu Leu Thr Gly Gly Lys Ser
                     85                  90                  95

Val Met Val Tyr Gly Gln Thr Glu Val Thr Arg Asp Leu Met Asp Ala
                100                 105                 110

Arg Ala Ala Ser Gly Ala Pro Ile Val Tyr Ser Ala Ser Asn Val Glu
            115                 120                 125

Leu His Glu Leu Lys Gly Glu Arg Pro Tyr Val Thr Phe Glu Lys Asp
        130                 135                 140

Gly Glu Arg Val Arg Val Asp Cys Asp Tyr Ile Ala Gly Cys Asp Gly
145                 150                 155                 160

Phe His Gly Val Ser Arg Lys Ser Ile Pro Glu Gly Val Leu Thr Glu
                165                 170                 175

Tyr Glu Arg Val Tyr Pro Phe Gly Trp Leu Gly Leu Ser Asp Thr
                180                 185                 190

Pro Pro Val His Glu Glu Leu Ile Tyr Ala His His Glu Arg Gly Phe
            195                 200                 205

Ser Leu Cys Ser Gln Arg Ser Leu Thr Arg Ser Arg Tyr Tyr Leu Gln
    210                 215                 220

Val Pro Leu Thr Asp Lys Val Glu Asp Trp Ser Asp Glu Arg Phe Trp
225                 230                 235                 240

Asn Glu Leu Lys Ala Arg Leu Pro Glu Asp Val Ala Ala Lys Leu Val
                245                 250                 255

Thr Gly Pro Ser Leu Glu Lys Ser Ile Ala Pro Leu Arg Ser Phe Val
                260                 265                 270

Val Glu Pro Met Gln Tyr Gly His Leu Phe Leu Val Gly Asp Ala Ala
                275                 280                 285

His Ile Val Pro Pro Thr Gly Ala Lys Gly Leu Asn Leu Ala Ala Ser
    290                 295                 300

Asp Val Cys Tyr Leu Tyr Arg Ile Leu Val Lys Val Tyr Arg Glu Gly
305                 310                 315                 320

Arg Thr Asp Leu Leu Glu Lys Tyr Ser Glu Leu Ala Leu Arg Arg Val
                325                 330                 335

Trp Lys Gly Glu Arg Phe Ser Trp Phe Met Thr Asn Leu Leu His Asp
                340                 345                 350

Phe Asp Gly His Lys Asp Ala Trp Asp Gln Lys Met Gln Gln Ala Asp
            355                 360                 365

Arg Glu Tyr Phe Leu Gly Ser His Ala Gly Leu Val Asn Ile Ala Glu
    370                 375                 380

Asn Tyr Val Gly Leu Pro Tyr Glu Asp Val Lys
385                 390                 395

(2) INFORMATION FOR SEQ ID NO:6:

(i) SEQUENCE CHARACTERISTICS:
        (A) LENGTH: 1446 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:
```

-continued

```
GATCAGCGCC GGCGCATGCG CCGCCGGCCA GCCATAACAG CGAGAGGGCT ATCCGCAATG      60

AAGACTCAAG TCGCCATCAT CGGCGCCGGT CCGTCCGGCC TCCTGCTCGG CCAGTTGCTG     120

CACAAGGCCG GCATCGACAA CGTGATCCTC AACGCCAGA CCCCGGACTA CGTGCTCGGC      180

CGCATCCGCG CCGGCGTGCT GGAACAGGGT ATGGTCGACC TGCTGCGCGA GGCCGGCGTC     240

GACCGGCGCA TGGCGCGCGA CGGGCTGGTC CACGAAGGCG TGGAGATCGC CTTCGCCGGG     300

CAGCGCCGGC GCATCGACCT GAAGCGCCTG AGCGGCGGCA AGACGGTGAC GGTCTACGGC     360

CAGACCGAGG TCACCCGCGA CCTCATGGAA GCCCGCGAAG CCTGCGGCGC CACTACCGTC     420

TACCAGGCCG CCGAGGTGCG CCTGCACGAC CTGCAAGGTG AGCGCCCCTA CGTGACCTTC     480

GAACGCGACG GCGAACGGCT ACGCCTGGAT TGCGACTACA TCGCCGGCTG CGATGGCTTC     540

CACGGCATCT CGCGGCAATC GATCCCGGCG GAGCGGCTGA AGGTCTTCGA GCGGGTCTAT     600

CCGTTCGGCT GGCTCGGCCT GCTCGCCGAC ACCCCGCCGG TCAGCCACGA ACTGATCTAC     660

GCCAACCATC CGCGCGGCTT CGCCCTGTGC AGCCAGCGTT CGGCGACCCG CAGCCGCTAC     720

TACGTACAGG TGCCATTGAC AGAGAAGGTC GAGGACTGGT CCGACGAGCG CTTCTGGACG     780

GAACTGAAAG CGCGCCTCCC GGCCGAGGTG GCGGAGAAAC TGGTGACCGG TCCTTCGCTG     840

GAGAAGAGCA TCGCGCCGCT GCGCAGCTTC GTGGTCGAGC CGATGCAGCA TGGCCGGCTG     900

TTCCTCGCCG GCGACGCCGC GCACATCGTG CCGCCCACCG GCGCCAAGGG ACTGAACCTG     960

GCGGCCAGCG ACGTCAGCAC GCTCTACCGG CTGCTGCTGA AGGCCTACCG CGAAGGGCGG    1020

GGCGAACTGC TGGAACGCTA CTCGGCAATC TGCCTGCGGC GGATCTGGAA GGCCGAACGC    1080

TTCTCCTGGT GGATGACTTC GGTGCTGCAT CGCTTCCCCG ACACCGACGC GTTCAGCCAG    1140

CGCATCCAGC AGACCGAACT GGAGTACTAC CTGGGCTCCG AGGCGGGCCT GGCGACCATC    1200

GCCGAGAACT ATGTCGGCCT GCCCTACGAG GAAATCGAGT AGGCCGCGCC ACCCCGGCGC    1260

AACGCCGGGG CACCGCTCCC AAGGCGGGAC GAACGTTGGC GCAGGCGAAT ATCGACGAAA    1320

GACGACCCTC GGACTTCGAT ATTCTCCGGC ACCTGTCCAT CCCCAGGCGC AGTATGATGC    1380

CCGTGCCTTC GCGTTCCGTC CGCCCAGGTG CCGCTCTTGT CCGATCTGCC AGAACCCGCC    1440

CGCCGT                                                               1446
```

(2) INFORMATION FOR SEQ ID NO:7:

(i) SEQUENCE CHARACTERISTICS:
        (A) LENGTH: 1315 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
AGGCTTTGTC GCAGTTTTCA CCTTCTTATG CTGCCCGCTC AAGTGAAAAA TGTCAGCCAT      60

AACACCAATG ACAACTCTTT CACTTGATCC GTTCGGGTGA AGCTTGCGAG CCATAAAAAT     120

AATGAAAACG CTAAAAACCC AAGTCGCCAT TATTGGCGCC GGTCCCTCCG GATTGCTGCT     180

CGGCCAGTTA CTGCACAACG CGGGTATCCA GACCCTGCTT CTAGAGCGCC AGAGCGCCGA     240

CTACGTGCAA GGCCGCATCC GTGCCGGGGT GCTGGAGCAA GGCATGGTCG ACCTGCTGCG     300

CGAAGCGGGC GTCAGCCGAC GCATGGACGC CGAGGGCCTT GTGCATGACG GTTTCGAATT     360

GGCACTCAAT GGCGAACTCA CCCACATCGA CCTCAAGGCG CTCACCGGCG CCAGTCGGT     420

GATGATCTAC GGCCAGACCG AAGTCACCCG TGACTTGATG GCCGCCCGCG AAGCGGCGGG     480
```

```
TGGCATCACT CTATACGAAA CGCAGAACGT GCAGCCTCAT GGTCACAAAA CTGATCGACC    540

CTGGCTGACC TTCGAGCACC AGGGTGAAGC TTTTCGCCTG GAGTGCGACT ACATCGCGGG    600

CTGTGATGGT TTTCACGGTG TGGCGCGGCA GTCGATTCCG GCGCAGTCGT TGAAGGTCTT    660

CGAGCGCGTC TATCCCTTCG GTTGGCTGGG CGTCCTCGCC GACACACCGC CGGTGCATGA    720

CGAACTGGTG TACGCCAAAC ATGCGCGTGG CTTTGCCCTG TGCAGCATGC GCTCGCCGAC    780

CCGCAGCCGC TATTACCTGC AAGTGCCGGT TGAAGAAGCG CTGGATGAAT GGTCGGATCA    840

GCGCTTCTGG GATGAGCTGA AAACCCGTTT GCCCAGTGCA CTGGCGGCCC AACTGGTCAC    900

CGGGCCATCC ATCGAGAAGA GCATCGCGCC CGCTGCGAGC TTTGAGGTCG AGCCGATGCA    960

ATACGGGCGC CTGTTCCTGC TGGGGACGC CGCGCATATC GTGCCGCCCA CCGGGGCCAA   1020

GGGCTTGAAC CTGGCGGCCA GCGACGTGAG TACGCTGTTT CGGATCTTGC TCAAGGTCTA   1080

TCGCGAGGGG CGGGTGGACC TGCTGGAACA GTACTCAGCG ATCTGCTTGC GCCGCGTATG   1140

GAAAGCCGAA CGGTTTTCCT GGTGGATGAC TTCGATGTTG CACCAGTTTC CGGAGGCCGA   1200

CGGGTTCAGC CAGCGCATTG CCGAGAGCGA GCTTGCGTAT TTCATCAGCT CCGAGGCGGG   1260

CCGCAAAACC ATCGCAGAAA ATTACGTCGG GCTTCCTTAC GAAGCTATCG AGTAG         1315

(2) INFORMATION FOR SEQ ID NO:8:

(i) SEQUENCE CHARACTERISTICS:
        (A) LENGTH:  394 amino acids
        (B) TYPE:  amino acid
        (C) STRANDEDNESS: Not Relevant
        (D) TOPOLOGY: Not Relevant (ii) MOLECULE TYPE:  protein (xi) SEQUENCE DESCRIPTION:  SEQ ID NO:8:

Met Lys Thr Gln Val Ala Ile Ile Gly Ala Gly Pro Ser Gly Leu Leu
1               5                   10                  15

Leu Gly Gln Leu Leu His Lys Ala Gly Ile Asp Asn Val Ile Leu Glu
            20                  25                  30

Arg Gln Thr Pro Asp Tyr Val Leu Gly Arg Ile Arg Ala Gly Val Leu
        35                  40                  45

Glu Gln Gly Met Val Asp Leu Leu Arg Glu Ala Gly Val Asp Arg Arg
    50                  55                  60

Met Ala Arg Asp Gly Leu Val His Glu Gly Val Glu Ile Ala Phe Ala
65                  70                  75                  80

Gly Gln Arg Arg Arg Ile Asp Leu Lys Arg Leu Ser Gly Gly Lys Thr
                85                  90                  95

Val Thr Val Tyr Gly Gln Thr Glu Val Thr Arg Asp Leu Met Glu Ala
            100                 105                 110

Arg Glu Ala Cys Gly Ala Thr Thr Val Tyr Gln Ala Ala Glu Val Arg
        115                 120                 125

Leu His Asp Leu Gln Gly Glu Arg Pro Tyr Val Thr Phe Glu Arg Asp
    130                 135                 140

Gly Glu Arg Leu Arg Leu Asp Cys Asp Tyr Ile Ala Gly Cys Asp Gly
145                 150                 155                 160

Phe His Gly Ile Ser Arg Gln Ser Ile Pro Ala Glu Arg Leu Lys Val
                165                 170                 175

Phe Glu Arg Val Tyr Pro Phe Gly Trp Leu Gly Leu Leu Ala Asp Thr
            180                 185                 190

Pro Pro Val Ser His Glu Leu Ile Tyr Ala Asn His Pro Arg Gly Phe
```

```
                195                 200                 205
Ala Leu Cys Ser Gln Arg Ser Ala Thr Arg Ser Arg Tyr Tyr Val Gln
    210                 215                 220

Val Pro Leu Thr Glu Lys Val Glu Asp Trp Ser Asp Glu Arg Phe Trp
225                 230                 235                 240

Thr Glu Leu Lys Ala Arg Leu Pro Ala Glu Val Ala Glu Lys Leu Val
                245                 250                 255

Thr Gly Pro Ser Leu Glu Lys Ser Ile Ala Pro Leu Arg Ser Phe Val
            260                 265                 270

Val Glu Pro Met Gln His Gly Arg Leu Phe Leu Ala Gly Asp Ala Ala
        275                 280                 285

His Ile Val Pro Pro Thr Gly Ala Lys Gly Leu Asn Leu Ala Ala Ser
    290                 295                 300

Asp Val Ser Thr Leu Tyr Arg Leu Leu Leu Lys Ala Tyr Arg Glu Gly
305                 310                 315                 320

Arg Gly Glu Leu Leu Glu Arg Tyr Ser Ala Ile Cys Leu Arg Arg Ile
                325                 330                 335

Trp Lys Ala Glu Arg Phe Ser Trp Trp Met Thr Ser Val Leu His Arg
            340                 345                 350

Phe Pro Asp Thr Asp Ala Phe Ser Gln Arg Ile Gln Gln Thr Glu Leu
        355                 360                 365

Glu Tyr Tyr Leu Gly Ser Glu Ala Gly Leu Ala Thr Ile Ala Glu Asn
    370                 375                 380

Tyr Val Gly Leu Pro Tyr Glu Glu Ile Glu
385                 390

(2) INFORMATION FOR SEQ ID NO:9:

(i) SEQUENCE CHARACTERISTICS:
        (A) LENGTH:  397 amino acids
        (B) TYPE:  amino acid
        (C) STRANDEDNESS: Not Relevant
        (D) TOPOLOGY: Not Relevant (ii) MOLECULE TYPE:  protein (xi) SEQUENCE DESCRIPTION:  SEQ ID NO:9:

Met Lys Thr Leu Lys Thr Gln Val Ala Ile Ile Gly Ala Gly Pro Ser
1               5                   10                  15

Gly Leu Leu Leu Gly Gln Leu Leu His Asn Ala Gly Ile Gln Thr Leu
            20                  25                  30

Leu Leu Glu Arg Gln Ser Ala Asp Tyr Val Gln Gly Arg Ile Arg Ala
        35                  40                  45

Gly Val Leu Glu Gln Gly Met Val Asp Leu Leu Arg Glu Ala Gly Val
    50                  55                  60

Ser Arg Arg Met Asp Ala Glu Gly Leu Val His Asp Gly Phe Glu Leu
65                  70                  75                  80

Ala Leu Asn Gly Glu Leu Thr His Ile Asp Leu Lys Ala Leu Thr Gly
                85                  90                  95

Gly Gln Ser Val Met Ile Tyr Gly Gln Thr Glu Val Thr Arg Asp Leu
            100                 105                 110

Met Ala Ala Arg Glu Ala Gly Gly Ile Thr Leu Tyr Glu Thr Gln
        115                 120                 125

Asn Val Gln Pro His Gly His Lys Thr Asp Arg Pro Trp Leu Thr Phe
    130                 135                 140

Glu His Gln Gly Glu Ala Phe Arg Leu Glu Cys Asp Tyr Ile Ala Gly
```

```
                145                 150                 155                 160
Cys Asp Gly Phe His Gly Val Ala Arg Gln Ser Ile Pro Ala Gln Ser
                165                 170                 175

Leu Lys Val Phe Glu Arg Val Tyr Pro Phe Gly Trp Leu Gly Val Leu
                180                 185                 190

Ala Asp Thr Pro Pro Val His Asp Glu Leu Val Tyr Ala Lys His Ala
                195                 200                 205

Arg Gly Phe Ala Leu Cys Ser Met Arg Ser Pro Thr Arg Ser Arg Tyr
                210                 215                 220

Tyr Leu Gln Val Pro Val Glu Glu Ala Leu Asp Glu Trp Ser Asp Gln
225                 230                 235                 240

Arg Phe Trp Asp Glu Leu Lys Thr Arg Leu Pro Ser Ala Leu Ala Ala
                245                 250                 255

Gln Leu Val Thr Gly Pro Ser Ile Glu Lys Ser Ile Ala Pro Ala Ala
                260                 265                 270

Ser Phe Glu Val Glu Pro Met Gln Tyr Gly Arg Leu Phe Leu Leu Gly
                275                 280                 285

Asp Ala Ala His Ile Val Pro Pro Thr Gly Ala Lys Gly Leu Asn Leu
                290                 295                 300

Ala Ala Ser Asp Val Ser Thr Leu Phe Arg Ile Leu Leu Lys Val Tyr
305                 310                 315                 320

Arg Glu Gly Arg Val Asp Leu Leu Glu Gln Tyr Ser Ala Ile Cys Leu
                325                 330                 335

Arg Arg Val Trp Lys Ala Glu Arg Phe Ser Trp Met Thr Ser Met
                340                 345                 350

Leu His Gln Phe Pro Glu Ala Asp Gly Phe Ser Gln Arg Ile Ala Glu
                355                 360                 365

Ser Glu Leu Ala Tyr Phe Ile Ser Ser Glu Ala Gly Arg Lys Thr Ile
                370                 375                 380

Ala Glu Asn Tyr Val Gly Leu Pro Tyr Glu Ala Ile Glu
385                 390                 395

(2) INFORMATION FOR SEQ ID NO:10:

(i) SEQUENCE CHARACTERISTICS:
        (A) LENGTH:  23 base pairs
        (B) TYPE:  nucleic acid
        (C) STRANDEDNESS:  single
        (D) TOPOLOGY:  linear (ii) MOLECULE TYPE:  other nucleic acid
        (A) DESCRIPTION:  /desc = "PRIMER"

(xi) SEQUENCE DESCRIPTION:  SEQ ID NO:10:

CARTTRCTNC AYAANGTNGG NAT                                                        23
```